United States Patent [19]
Steiner et al.

[11] Patent Number: 5,868,680
[45] Date of Patent: Feb. 9, 1999

[54] QUANTITATIVE CHARACTERIZATION OF FIBRILLATORY SPATIOTEMPORAL ORGANIZATION

[75] Inventors: Paul R. Steiner; Michael D. Lesh, both of Mill Valley, Calif.

[73] Assignee: The Regents of the University of California, Oakland, Calif.

[21] Appl. No.: 936,083

[22] Filed: Sep. 23, 1997

[51] Int. Cl.$^6$ .......................... A61B 5/046; A61B 5/0402
[52] U.S. Cl. ................................ 600/518; 600/515; 607/5
[58] Field of Search ..................................... 600/518, 515; 607/5

[56] References Cited

U.S. PATENT DOCUMENTS

| | | |
|---|---|---|
| 4,354,497 | 10/1982 | Kahn . |
| 4,790,317 | 12/1988 | Davies ........................................ 607/5 |
| 4,799,493 | 1/1989 | DuFault . |
| 4,974,598 | 12/1990 | John . |
| 5,058,599 | 10/1991 | Andersen . |
| 5,107,850 | 4/1992 | Olive . |
| 5,158,079 | 10/1992 | Adams et al. . |
| 5,366,486 | 11/1994 | Zipes et al. ................................ 607/5 |
| 5,366,487 | 11/1994 | Adams et al. . |
| 5,366,587 | 11/1994 | Adams et al. . |
| 5,400,796 | 3/1995 | Wecke . |
| 5,439,483 | 8/1995 | Duong-Van . |
| 5,464,431 | 11/1995 | Adams et al. . |
| 5,476,503 | 12/1995 | Yang . |
| 5,549,641 | 8/1996 | Ayers et al. . |
| 5,605,159 | 2/1997 | Smith et al. . |
| 5,676,153 | 10/1997 | Smith et al. . |

FOREIGN PATENT DOCUMENTS 617 980 A2  10/1994  European Pat. Off. .

Primary Examiner—William E. Kamm
Assistant Examiner—Carl H. Layno
Attorney, Agent, or Firm—John P. O'Banion

[57] ABSTRACT

Described is a method for monitoring the spatiotemporal organization of atrial arrhythmias, especially atrial fibrillation, based on an analysis of sequences of activation patterns obtained from a particular set of atrial recording sites. This analysis measures the degree of order change in the sequence of activation patterns, or of the time between order changes. Electrogram signals produced by atrial fibrillation are acquired simultaneously from sites adjacent to atrial tissue using multipole electrode catheters. These signals subsequently are filtered and processed to obtain a group of time series which manifest peaks at the latencies of maximal energy in the original data; when these peaks occur are the latencies that are defined as activation events. The activation events from each sampled site are ordered with respect to activation events from each of the other sites, and are translated into corresponding activation patterns, which are determined by the specific spatiotemporal activation sequence associated with each activation event. Each activation pattern in the sequence then is compared with subsequent observed patterns to determine if any spatiotemporal order change has occurred, and if so, to what extent; also, the distribution of observed activation patterns is evaluated for an additional characterization of atrial fibrillation.

54 Claims, 12 Drawing Sheets

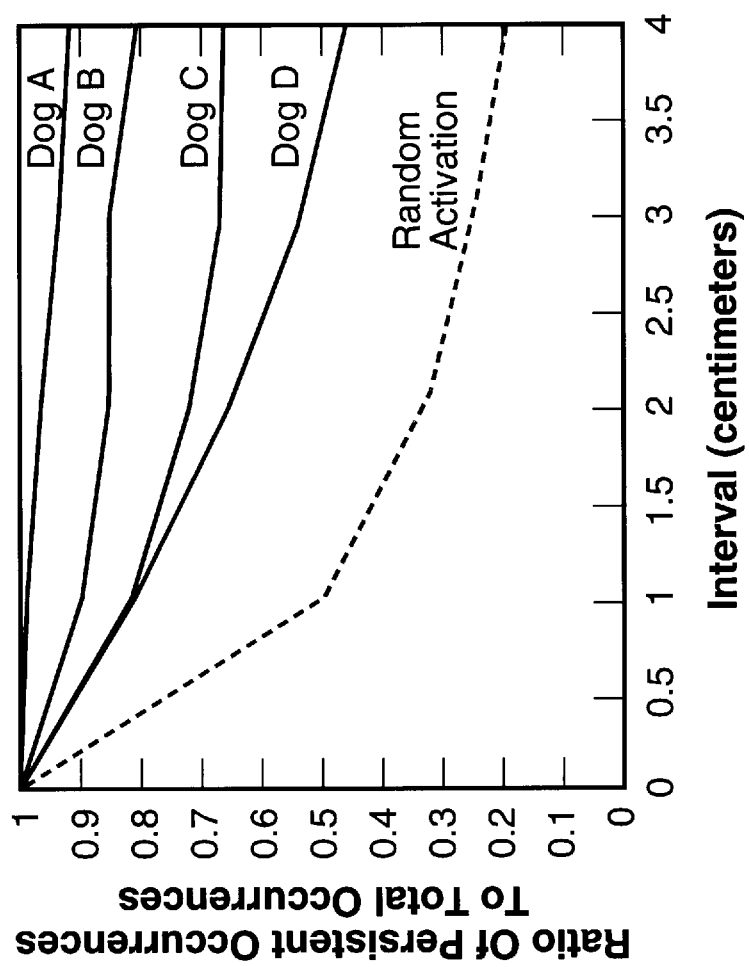
FIG. −7

QUANTITATIVE CHARACTERIZATION OF FIBRILLATORY SPATIOTEMPORAL ORGANIZATION

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention pertains generally to the characterization of atrial fibrillation by quantifying the spatiotemporal organization (STO) of electrical propagation during atrial fibrillation, and to using such STO to direct therapy.

2. Description of the Background Art

Atrial fibrillation is the most common sustained cardiac arrhythmia encountered in clinical practice, and affects as many as 5% of Americans over the age of 65. Atrial fibrillation is associated with symptoms such as palpitations, shortness of breath, and fatigue. In addition, it is associated with significant morbidity and mortality, including embolic stroke and symptoms related to loss of atrial mechanical function and atrioventricular synchrony. Furthermore, therapy commonly used in the treatment of atrial fibrillation also has the potential for significant morbidity and mortality. For example, antiarrhythmic therapy can result in proarrhythmia, whereas coumadin therapy may result in hemorrhagic complications.

Despite the high incidence of atrial fibrillation, its underlying mechanisms are not well understood. Around the turn of this century, several researchers suggested that atrial fibrillation was the result of single or multiple ectopic foci. In the 1920s, Lewis and Garrey suggested that a different mechanism, based on re-entry set up by localized areas of conduction block, instead might be responsible for the chaotic nature of electrograms recorded during atrial fibrillation.

In 1962, Moe published his widely known multiple wavelet hypothesis of atrial fibrillation. Moe said that the atria were fibrillating "when records of their electrical activity show rapid oscillations of irregular contour and duration, or when synchronous organized mechanical activity is replaced by fine irregular ripples, coursing without apparent pattern over the atrial surface." He also stated that any factor reducing the number of circulating wavelets will tend to increase the chances for spontaneous recovery. Moe's hypothesis of multiple circulating wavelets later was verified by Allessie and coworkers who used high-density epicardial mapping to evaluate atrial fibrillation. They noted that fibrillatory waveforms showed a temporal variation in cycle length at a given site and a spatial variation in cycle length at a given time.

At present there is a critical shortage of techniques for evaluation of atrial electrophysiologic substrate in patients prone to atrial fibrillation. This shortage results from two factors: first, analysis of fibrillatory electrograms is complicated by continual spatial and temporal variations in activation patterns and, second, detailed characterization of fibrillation typically requires measurement from a large number of endocardial or epicardial recording sites this is not practical for implementation in the cardiac electrophysiology laboratory or by an implanted device.

Past and present efforts to better understand the electrophysiology of patients with atrial fibrillation can be broken down into four categories: assessment of atrial vulnerability, related efforts in measurement of organization of ventricular fibrillation, measurement of organization in atrial fibrillation, and assessment of propagation direction.

Assessment of Atrial Vulnerability

The use of programmed stimulation in an attempt to induce atrial fibrillation has been used by several groups to evaluate susceptibility to fibrillation. A study by Fujiki demonstrated that patients with paroxysmal atrial fibrillation and vulnerable atria (defined as induction of repetitive atrial firing due to a single atrial extrastimulus) had shorter atrial effective refractory periods (ERPs) than patients without atrial vulnerability. Electrograms of the premature beat were also longer and more fractionated in patients with atrial vulnerability. The future clinical implications of measurement of atrial vulnerability remain unclear.

Measurement of Organization in Ventricular Fibrillation

The concept of measuring the spatiotemporal organization of arrhythmias has been explored more extensively in the case of ventricular fibrillation than in atrial fibrillation. Ropella and coworkers compared the magnitude-squared coherence (MSC), ventricular rate, and irregularity of cycle length during induced ventricular arrhythmias. Differentiation of monomorphic ventricular tachycardia (VT) from polymorphic VT was possible using MSC, more difficult using ventricular rate, and not possible using beat-to-beat irregularity. Sih and coworkers computed pair-wise values of MSC from an array of unipolar electrodes. They noted that MSC decreased as a function of distance for all investigated rhythms, but the most pronounced effects were in the case of fibrillation. Bayly and coworkers measured correlation length in pigs during ventricular fibrillation and found that correlation length varied with the duration of fibrillation. Damle et al. analyzed the effects of chronic and subacute infarction on the organization of ventricular fibrillation in dogs. The degree of linking was lower in the animals without an infarction, suggesting a lower degree of organization during ventricular fibrillation.

Measurement of Organization in Atrial Fibrillation

Early analysis of atrial fibrillation was limited to characteristics of the surface electrocardiogram. Subsequent efforts categorized endocardial electrograms on the basis of morphology, average rates of local activation, rate variance, and distribution of activation intervals. Wells and coworkers recorded epicardial bipolar electrograms in patients developing atrial fibrillation following cardiac surgery. They found that it was possible to categorize the fibrillation into four types on the basis of electrogram organization and morphology. Konigs and coworkers described three types of atrial fibrillation in patients according to the number of circulating wavelets present in patients undergoing surgery for Wolf-Parkinson-White Syndrome. Although this study provided evidence for varying degrees of organization of fibrillation between different patients, it did not evaluate temporal variations in individual patients.

Botteron and Smith computed an activation space constant from endocardial electrogram recordings. Their work is notable because it goes beyond simple analysis of temporal characteristics of electrograms. Instead, it attempts to fit the measured spatial and temporal data to a single function, from which a descriptive spatial statistic is obtained. The function, which takes distance and time gradients as time-dependent variables, is an exponentially decaying curve of cross-correlation coefficients. This approach is based on the expectation that signals will be less correlated when acquired from sites separated by greater distances. They found that the spatial scale of atrial organization was shorter in patients with chronic fibrillation, longer in patients with newly acquired fibrillation, and of an intermediate value in patients with a history of paroxysmal atrial fibrillation.

Measurement of Propagation Direction

Other groups have examined direction of propagation during fibrillation. Gerstenfeld et al. used an orthogonal catheter to demonstrate that the relative direction of atrial activation could remain constant for six or more consecutive atrial activations. This finding showed that not only is atrial reentry likely, but that it has time-varying degrees of spatial organization, presumably the result of the combination and destruction of individual wavelets. Recently, Holm and coworkers also investigated propagation direction using bipolar electrograms recorded from 56 epicardial locations. They found three types of preferable activation patterns and discovered that focal atrial activation occurred as a repetitive phenomenon.

Despite the extensive research noted above, there is a clear lack of tools to assist the clinician in determining which of these treatment strategies is best suited for a given patient. This problem is likely to be compounded as new treatments continue to emerge. In addition to the immediate need for optimizing patient treatment, there is a longer-term need for a better understanding of the electrophysiological mechanisms responsible for atrial fibrillation. The present invention satisfies those needs, as well as others, and overcomes the drawback of prior detection methodologies that rely on a large number of epicardial recording sites to quantify spatiotemporal organization and which are not feasible in the cardiac electrophysiology laboratory or for implementation by implanted devices.

BRIEF SUMMARY OF THE INVENTION

The present invention pertains to a method for monitoring activation sequences of a particular set of recording sites and, based on a measure of the degree of order change or of the time between order changes, determining spatiotemporal organization (sequences of activation patterns) for characterization of atrial fibrillation.

In accordance with an aspect of the invention, a new class of metrics have been developed for analysis of endocardial electrograms recorded during atrial fibrillation. This new class of metrics is based on the premise that organized rhythms (like sinus and flutter) seldom change activation pattern within a specified atrial region, but disorganized rhythms (like fibrillation) change activation pattern frequently. By representing the electrogram data as a sequence of discrete spatiotemporal patterns generated from the ordered local activation events taken from a regional set of electrodes, rather than relying upon the conventional method of representing the data as a set of waveforms, the degree of order change and the amount of time between order changes can be measured in an efficient manner. The invention involves an effective data reduction technique that nonetheless permits a thorough analysis of spatiotemporal activation sequences with limited computational overhead, an important factor when considering real-time applications in a laboratory setting or for device-based implementations. Furthermore, these event-based metrics are robust when dealing with noisy data, enable a near-instantaneous assessment of spatiotemporal organization, do not depend inherently on mean activation rates, do not require statistical stationarity, and facilitate analysis of data recorded from unevenly spaced electrodes. And, unlike qualitative approaches based on visual appearance and classification of fibrillation into predefined categories, these event-based metrics provide a quantitative measure of organization of electrical activity specific to targeted atrial anatomic regions.

By way of example, and not of limitation, in accordance with the invention, electrogram signals produced by atrial fibrillation are acquired from sites adjacent to the atrial endocardium using multipole electrode catheters. The acquired signals subsequently are screened to remove those signals having high noise levels or extremely poor signal quality as a result of a bipole lying over an orifice or making poor contact with the endocardial surface. These screened signals are then processed to obtain the local activation latencies at each site in the regional spatial set under consideration. One manner by which this is accomplished is to convert each original acquired signal into a time series having peaks at or near the latencies of maximal energy within a specified upper frequency bandwidth; these peaks are accepted as occurring at time latencies that define activation events. Next, the activation events associated with the epoch of simultaneously acquired atrial fibrillation signals are sequenced according to temporal order, irrespective of their spatial location in the region, to create a sequence of activation events. Then, for each activation event within the epoch, the temporal order of the nearest subsequent activation event latency at each of the other sites within the set is noted in association with a consistent spatial ordering of sites, resulting in an activation pattern. Once this is accomplished in sequence for each activation event of the epoch, a sequence of activation patterns exists.

In accordance with an aspect of the invention, and in order to facilitate the comparison of all activation patterns in this epochal sequence, it is helpful to convert the activation patterns to a common spatiotemporal reference within the set; this process involves a simple modulo operation. A finite set of unique activation patterns translated in this manner exists, and these are referred to as the spatiotemporal patterns. For activation pattern analysis in the region covered by a linear set of N electrodes on a multipolar catheter, for example, the site associated with the most proximal electrode could be assigned to be the spatial reference, and the translation would convert the pattern to reflect the first activation event to exist at this site within each activation pattern. For N sites, there are a total of N! possible activation patterns that theoretically may be detected, which translate into (N—1)! unique spatiotemporal patterns; for each distinct spatiotemporal pattern, there exists N possible activation patterns, and these differ only with respect to which site is labeled first in the associated activation patterns.

By way of example, and not of limitation, in accordance with aspects of the invention, the sequences of activation patterns and their associated spatiotemporal patterns may be used to characterize regional spatiotemporal organization of fibrillation, which can be quantified using metrics which fall into three basic classes:

(1) Persistence of Activation Patterns

Whenever the sequence of spatiotemporal patterns manifests repetition of a specific spatiotemporal pattern (or even a subset of patterns across a subregion), fibrillatory organization is evident. Persistence refers to the characteristic whereby two spatiotemporal patterns in sequence remain unchanged, which is a reflection of organization. For example, consider a group of five endocardial sites being activated in an utterly random fashion (without regard to constraints imposed by refractory periods, anisotropy, etc.):

approximately one fifth of the time, a successive spatiotemporal pattern within the sequence of patterns would be classified as being persistent. The spatiotemporal pattern sequence of a perfectly organized rhythm remains persistent throughout the entire sequence epoch. The general degree of spatiotemporal organization of an atrial region during fibrillation can be quantified by measuring the degree of persistence that exists between these two extremes. The persistence index represents the ratio of persistent increments of the spatiotemporal pattern sequence to the total number of spatiotemporal pattern increments within the entire sequence. The mean persistence represents the average number of consecutive increments of the spatiotemporal pattern sequence that remain persistent within a specified epoch.

An alternative way in which to consider the sequential spatiotemporal pattern data is to quantify the amount of change that occurs between manifest patterns in association with each increment of the epochal sequence. For N sites, there are N degrees of order change ranging in magnitude from 0 to (N−1) position shifts that can occur from one spatiotemporal pattern to the next. This allows for a discrete disorganization metric that records the amount of spatiotemporal disorder, and at a relatively high temporal resolution that is determined by the number of regional electrodes and the frequency of activations at each of the electrode sites—for each detected event anywhere within the region, a new value quantifying spatiotemporal pattern flux can be obtained. Furthermore, related to the disorganization metric is the asynchrony metric, which quantifies from one activation pattern to the next the magnitude of the total change in the latency intervals between all possible pairs of regional sites. This metric is intended to provide a regionalized view of the fibrillatory process that has a relatively high temporal resolution, is independent of fibrillatory rate, and makes no assumptions about statistical stationarity of activation events.

(2) Activation Pattern Distributions

In addition to examining spatiotemporal pattern sequences, the observed statistical distributions of spatiotemporal patterns can be examined for additional insight regarding the spatiotemporal organization of fibrillatory activations. In probabilistic terms, an equal distribution of spatiotemporal patterns would be expected to be detected across a regional grouping of electrodes, assuming the following conditions: (1) at each site the fibrillatory activations are utterly random; (2) local activation latencies are detected accurately; and (3) the acquisition epoch is of sufficient duration. Assuming the latter two conditions, deviation from an observed random distribution of spatiotemporal patterns would reflect a degree of order, and an analysis of the statistical distributions of these patterns thereby would provide information regarding the organization of atrial fibrillation in the region of the electrodes. Certain spatiotemporal patterns may be observed to predominate over other patterns within the entire range of possible spatiotemporal patterns associated with a defined spatial set. For instance, if propagation is predominantly in one direction along a multipole catheter, it will be reflected by a predictable uneven distribution of specific spatiotemporal patterns. Analytic capability of this nature in the clinical laboratory ultimately may permit fibrillatory mapping to identify specific foci or re-entrant circuits that potentially may play a role in sustaining fibrillation.

(3) Activation Pattern Trajectories

The methodology of the proposed invention imposes a finite number of possibilities for what activation patterns can follow from other specific activation patterns. Furthermore, the sequence of activation patterns may be nonrandom in other ways, as for example if there is a propensity for certain activation patterns to evolve from another specific activation pattern, rather than from a random distribution of the patterns. Even if a full range of evenly distributed activation patterns were to be manifest during fibrillation, a degree of order from within a region yet may be detectable by virtue of a higher order analysis of the epochal sequence of activation patterns. Rather than analyzing the occurrence of specific activation patterns, manifest sequences of activation patterns may be analyzed; this is referred to as pattern trajectory analysis. An activation pattern emerging from, or dissipating into, a subsequent activation pattern of the epochal sequence is the simplest manifestation of a first order activation pattern trajectory; a finite number of 1st order trajectories exists for a specified number of spatial sites sampling a region of interest. An analysis of the manifest sequence of 1st order trajectories, as well as the associated statistical distributions of these 1st order trajectories, provides yet another means for characterizing the spatiotemporal organization of fibrillation.

In fact, within the limitations imposed by the epoch length of the acquired signals and the accuracy with which the activation events accurately reflect the true local activation latencies at the regional sites sampled, similar analyses may be accomplished for higher order trajectory analyses. Greater insight into the structure of fibrillatory STO may be obtained through the combination of various trajectory analyses of different order. This information, perhaps in combination with similar analyses from other atrial regions, in some instances may ultimately allow for a specific enough characterization of atrial fibrillation to allow for reasonably accurate short-term predictions of subsequent activation patterns to become manifest next in the sequence of patterns.

Accordingly, the present methodology described for this invention provides a compact, flexible, and powerful framework for the analysis of fibrillatory STO, which ultimately may assist the clinician in evaluating treatment options, guiding specific interventions, and obtaining a better understanding of the mechanisms of atrial fibrillation.

An object of this invention is to characterize both qualitatively and quantitatively the spatiotemporal organization of atrial fibrillation.

Another object of the invention is to understand the relationship between atrial structure, anatomic and functional block, and the spatiotemporal organization of fibrillation.

Another object of the invention is to provide an event-based analysis of spatiotemporal organization that functions independent of atrial activation rate.

Another object of the invention is to facilitate statistical analysis of different arrhythmic episodes by evaluating between the defined statistical extremes of perfect order and purely random local activation distributions.

Another object of the invention is to provide for compact data representation (data can be translated into the time domain by replacing the activation event sequence with associated temporal latencies).

Another object of this invention is to allow for its ubiquitous implementation in modern clinical electrophysiology laboratories by making it adaptable to a wide variety of commercially available catheters and data acquisition equipment.

Another object of the invention is to provide for robust operation when dealing with noisy signals (like those often observed in endocardial recordings of atrial fibrillation).

Another object of this invention is to introduce certain metrics that reflect spatiotemporal organization of atrial fibrillation without requiring the assumption of statistical stationarity or pseudostationarity of signal time series.

Another object of this invention is to provide flexibility to implement high order analyses of the spatiotemporal organization of activation pattern sequences, as another avenue of characterizing spatiotemporal order.

Another object of this invention is to permit an evaluation of the spatiotemporal organization of fibrillatory activation, with the finest temporal resolution realizable for a specified set of simultaneously sampled spatial sites; such a realization is sought so as to enhance the feasibility of the near real-time determination of fibrillatory spatiotemporal organization.

Another object of the invention is to support an analysis of signals from groups of bipoles that are unevenly distributed in the atrium.

Another object of the invention is to identify specific atrial regions through which the propagation of wavefronts during fibrillation is most highly organized, and similarly to identify regions through which the propagation of wavefronts during fibrillation is most disorganized.

Another object of the invention is to allow a clinician to determine the relative degrees of spatiotemporal organization in both left and right atria, and regions thereof.

Another object of the invention is to understand organizational changes in fibrillation as patients progress from paroxysmal to chronic fibrillation.

Another object of the invention is to identify patients who will be more likely to respond to specific antiarrhythmic drugs.

Another object of the invention is to guide longitudinal evaluations of the effect of medications on atrial fibrillation.

Another object of the invention is to guide longitudinal evaluations of the effect of surgical or ablative lesions on atrial fibrillation.

Another object of the invention is to identify patients who are candidates for an implantable atrial defibrillator.

Another object of the invention is to detect atrial fibrillation.

Another object of the invention is to trigger either a temporary or permanently implanted defibrillation device when the metrics indicate a specific spatiotemporal organization characteristics to increase the likelihood of a successful defibrillation attempt for a given level of delivered energy.

Another object of the invention is to identify patients who are appropriate for catheter ablation and to identify those regions of the atrial that may be targeted for transcatheter ablation in an effort to decrease the propensity for fibrillation to sustain.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1A through FIG. 1C depict simultaneous 4-second epochs of atrial fibrillation that were acquired from different right atrial regions using bipoles with 1 millimeter interelectrode spacing, and are from the anterolateral, septal, and posterolateral right atrium, respectively. FIG. 1D depicts a simultaneously acquired surface electrogram.

FIG. 2A illustrates a 2 second epoch of an electrogram obtained from site X in an anterolateral right atrial region. FIG. 2B depicts the time series resulting from the process of high pass filtering, signal rectification, and subsequent smoothing via low pass filtering; peaks of the resultant time series estimate the local activation latencies detected via the bipole positioned at site X. Activation event latencies are represented by the vertical dashed lines that occur at said peaks, and extend to FIG. 2C, which depicts a sequence of activation events corresponding to the local activations determined for site X.

FIG. 3A illustrates the derivation of an activation pattern for the first activation event (occurring at site L) in the epochal sequence; for a specified spatial ordering of sites {JKLMN} initiated by said activation event, the temporal order of activation events among the sites is {24135}. FIG. 3B illustrates the derivation of the activation pattern after an increment to the second activation event (occurring at site J) in the epochal sequence; for a specified spatial ordering of sites {JKLMN} initiated by said activation event, the temporal order of activation events among the sites is {13524}. Note that only one activation event is considered per site, and every site is included in obtaining a pattern. FIG. 3C through FIG. 3E depict the derivation of activation patterns after incrementing the epochal sequence to the third, fourth, and fifth activation events, respectively.

FIG. 4A through FIG. 4F are graphs illustrating related activation patterns and show activation event sequences for a regional set of sites [J,K,L,M,N], with the activation event sequence for each site obtained as depicted in FIG. 2A through FIG. 2C. Activation events from all sites are placed according to the order of their associated activation latencies into an epochal sequence, which is depicted at the bottom of each panel. Each activation event has an associated activation pattern. Each of FIG. 4A through FIG. 4F depicts an epoch in which the manifest spatiotemporal pattern does not change, despite the different activation patterns. Note, however, that FIG. 4A and FIG. 4F depict the same activation pattern, whereas FIG. 4B through FIG. 4E depict all related activation patterns associated with the one spatiotemporal pattern. These are obtained by incrementing through the epochal sequence.

FIG. 5A depicts an arbitrary activation pattern for a regional set of sites [J,K,L,M,N]; the arbitrary pattern in this case is the same as the one in FIG. 4A. The first activation event of an arbitrary activation pattern (in this example, at site L) is replaced by the next activation event at the same site in the emerging activation pattern; this subsequent activation event may emerge anywhere in the temporal order of activation events of the remaining sites, but the order of these remaining sites with respect to each other is unchanged. FIG. 5B illustrates the emergence of a related activation pattern, as in FIG. 4B; the number of activation events in the emerging activation pattern that occur before the successive activation event at site L is 4. FIG. 5C through FIG. 5F illustrate other possible positions for the next activation event at site L. In FIG. 5C, the number of activation events in the emerging activation pattern that occur before the successive activation event at site L is 3, resulting in a different activation pattern emerging from the preceding activation pattern depicted in FIG. 5A. In FIG. 5D and FIG. 5E, the number of activation events in the emerging activation pattern that occur before the successive activation event at site L is 2 and 1 respectively, resulting in two other distinct activation patterns emerging. In FIG. 5F the number of activation events in the emerging activation pattern that occur before the successive activation event at site L is 0, but in this case, the same activation pattern emerges. Consequently, for a set of 5 sites, the activation pattern emerging from any arbitrary activation pattern is constrained to be one of only 5 activation patterns (including the arbitrary pattern).

FIG. 7 is a graph showing persistence curves (using epochal sequence increment=1) for four different dogs (A, B, C and D), each having a different degree of arrhythmia "coarseness" ranging from a rapid atypical flutter (Dog A) to fine atrial fibrillation (Dog D), with the dashed line showing the expected ratio of persistent activation patterns based on a statistical model of purely random local activation distributions.

DETAILED DESCRIPTION OF THE INVENTION

Computation of fibrillation organization metrics in accordance with the present invention is a multi-step process involving signal acquisition, event detection, derivation of activation patterns, translation of activation patterns to spatiotemporal patterns, pattern sequence analysis, and pattern distribution analysis as described herein.

Signal Acquisition

Figure 1A:
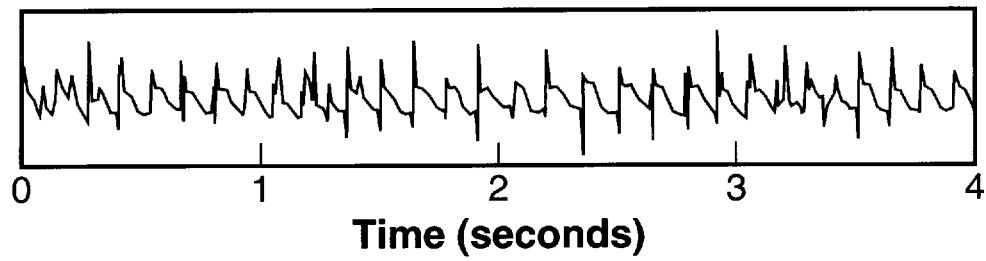
FIG. 1A through FIG. 1D are graphs illustrating data from simultaneous epochs of atrial fibrillation.
Figure 1B:
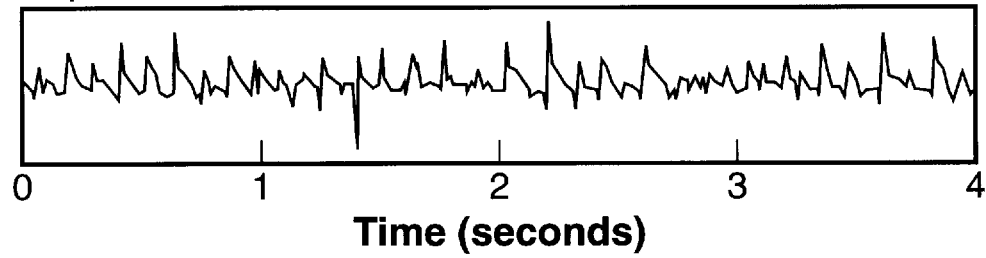
Figure 1C:
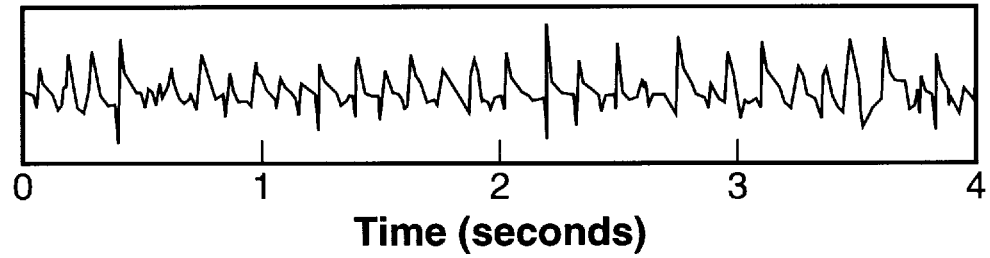
Figure 1D:
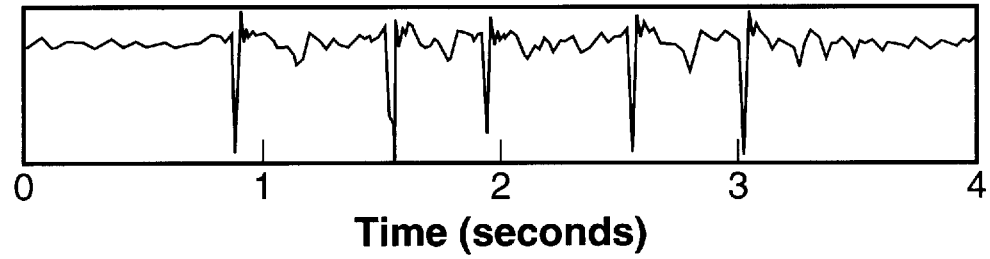

Acquisition of electrograms during atrial fibrillation can be accomplished using multipole electrode catheters for which electrode spacing is known (basket catheters, standard mapping catheters, or implanted electrode leads are supported). Specifically, open chest techniques for signal acquisition are not required. The methodology relies upon the ability to approximate local activation times at each site associated with a set of spatially-distributed electrodes. Although this can be accomplished with a variety of electrode configurations (unipolar, bipolar, quadripolar, etc.), multipole catheter configurations having 1–2 mm spacing between the bipole elements are ubiquitous, and commonly are employed in clinical laboratories for temporary insertion during electrophysiology studies; permanently implanted electrodes also could be employed. The signals of the spatial set simultaneously are acquired at a sampling rate sufficient to avoid aliasing of atrial signals; again, data acquisition systems available in modern clinical electrophysiology laboratories commonly can be configured to sample multiple signals at 1 KHz over a voltage range large enough to avoid saturation of the preamplifiers (up to±160 mV, preferably with at least 12-bit resolution) within a 0.5–250 Hz bandwidth (or greater). Signals may be acquired from sites adjacent to targeted atrial regions; typically these regions will be endocardial sites, but also they may be from epicardial sites, or from positions close to atrial tissue targeted for mapping (i.e. from inside the coronary sinus, pulmonary arteries, pericardial space, or esophagus). Catheter positioning is aided by various imaging modalities, such as biplane fluoroscopy or intracardiac echocardiography. FIG. 1A through FIG. 1D illustrate examples of simultaneously acquired atrial signals during a 4-second epoch of atrial fibrillation using catheters positioned endocardially, having bipoles with 1 millimeter (mm) inter-electrode spacing; FIG. 1A through FIG. 1C illustrate electrograms from different right atrial regions, and FIG. 1D shows an associated surface lead.

During acquisition, signals are screened to identify those that have high noise levels or extremely poor signal quality as a result of, for example, an electrode positioned over an orifice or an electrode making poor contact with the endocardial surface. Screening can be performed in many conventional ways, including visual or other forms of manual screening, as well as automatically using an algorithm or the like. If a faulty signal is identified, electrode position can be adjusted for a better sampling of the targeted atrial region, or eliminated from the analysis (perhaps substituting a signal from an alternate bipole).

Event Detection

In order to assess activation sequences, the ability to accurately estimate the latencies of local atrial tissue activation under a variety of signal conditions is critical. The specific technique chosen for detecting local activations should be dictated by the properties of the signals acquired, and the circumstances under which they were acquired: the methodology for this invention requires an estimation of local activation latencies at each site associated with the set of electrodes positioned at the region of interest, and the methodology is flexible enough to employ the most appropriate local activation detection scheme for a given set of signals. For instance, if unipolar signals are acquired, the detection of local activation latencies is apt to be optimized using an algorithm different from one employed for signals acquired when using 1 mm bipoles.

Figure 2A:
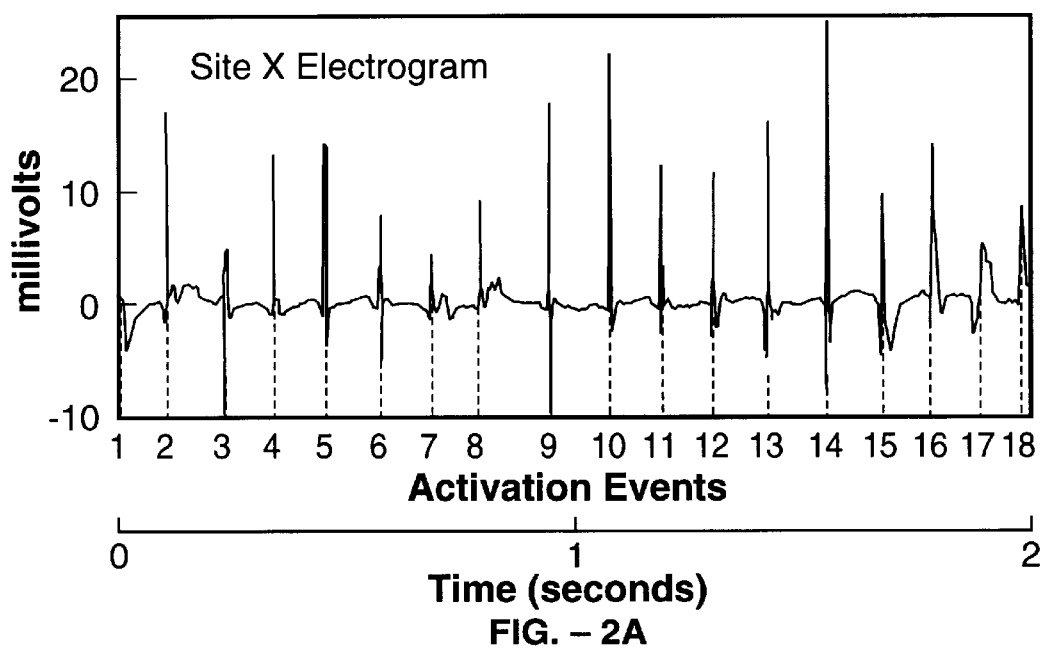
FIG. 2A through FIG. 2C are graphs illustrating activation event detection.
Figure 2B:
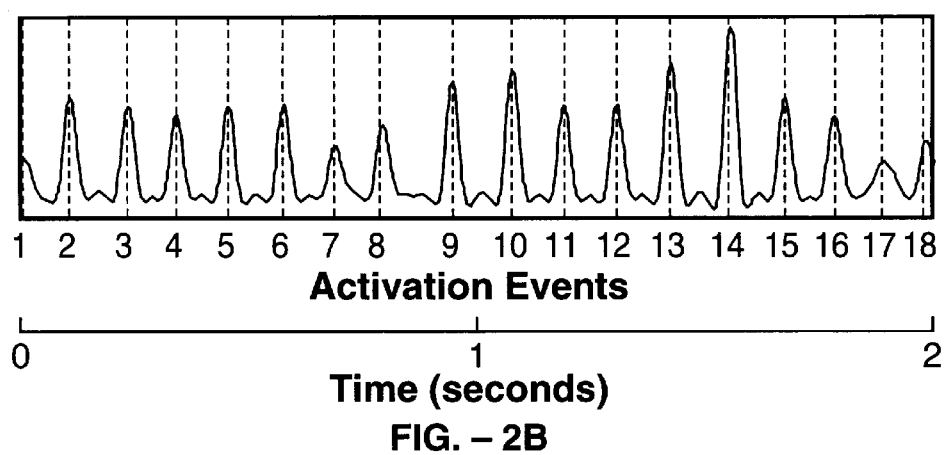
Figure 2C:
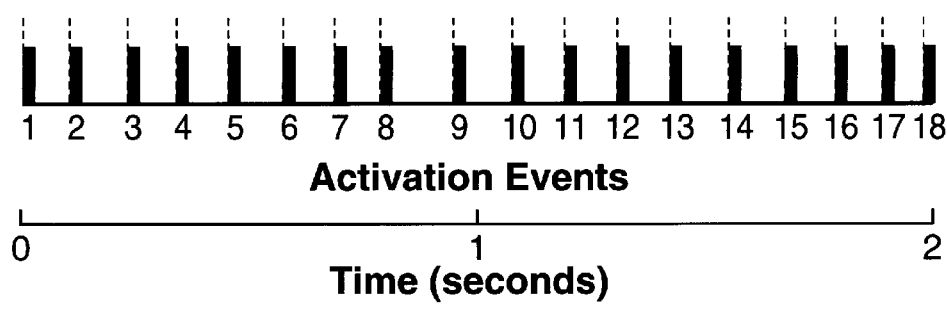

Consider the example of signals acquired using multiple 1 mm bipoles distributed at 1 cm intervals along a catheter, positioned parallel to the tricuspid annulus and adjacent to the anterolateral endocardial region of the right atrium. These signals may be (1) highpass filtered to isolate out upper bandwidth signal content, (2) modified via rectification to accentuate such content nonlinearly, and then (3) smoothed via a lowpass filtering operation at a cut-off frequency value that is half of that used for the high-pass frequency cut-off. The result is a smoothed time series having peaks at the latencies of maximal upper bandwidth energy in the original data, and said peaks have been observed to correspond well to the latencies of local activations, as depicted in FIG. 2A and FIG. 2B for one site. For each acquired raw signal in the set, these latencies then are associated with a sequence of activation events, shown in FIG. 2C; an activation event refers to the detection of a local activation of tissue.

In one variation of this method, prior to signal rectification, first order differentiation is accomplished to further enhance the upper bandwidth transients most likely to be associated with localized depolarizing activity. The filtering should be implemented in a manner such that any phase shift of upper bandwidth signal content is minimized; for example, if IIR filters are employed, bidirectional filtering is desirable. While various filter limits can be employed, it has been found that for endocardial signals acquired using 1 mm bipoles, high pass cut-off frequencies in the range of 32–64 Hz and low pass cut off frequencies in the range of 12–24 Hz provide optimal results, with specific cut-off values depending on a variety of factors, including the minimum local activation cycle lengths manifest. Upper bandwidth energy that is less concentrated along the temporal axis tends to be noise, and far field signals lack the upper bandwidth energy content relative to the strength of upper bandwidth energy content for local signals. These factors contribute to a robust event detection scheme for endocardial signals acquired using narrow bipole spacing, such as the 1 mm bipole distance cited above.

Derivation of Activation Patterns

Once the latencies of activation events have been determined at each site within the atrial region of interest, activation patterns are derive for use in a subsequent characterization of fibrillatory spatiotemporal structure. One technique for generating the activation patterns requires that every activation event detected in the region, irrespective of the site at which said events were detected, be placed together in a sequence whose order is determined by the temporal latency associated with each activation event; this sequence is referred to as an epochal sequence of activation events. This is depicted in FIG. 3A through FIG. 3E, at the bottom of each panel. Next, an activation pattern is determined for each activation event in this epochal sequence. This may be accomplished by specifying that each activation event is the first event in its associated activation pattern, and the temporal order of the next activation event at each of the other sites in the region subsequently is noted. The result is a epochal sequence of activation patterns, with each activation pattern representing a temporal ordering of activation events for a specified and consistent spatial ordering of sites in the region. Increments of the epochal sequence are depicted in FIG. 3A through FIG. 3E, and in each case, for the spatial ordering {JKLMN}, an associated temporal ordering of activation events among these sites is obtained; for each increment in the epochal sequence, another activation pattern is noted.

More generally, activation patterns can be determined according to the order of spatial location of the activation events (for a consistent temporal order of those events), or by the temporal order of the activation events (for a consistent spatial order of those events). The two ordering techniques simply are two different ways of representing the same information and can be used interchangeably. We arbitrarily chose to use a labeling scheme that reflects the varying temporal order of the activation events within the sequence of activation patterns.

The temporal resolution for analyzing spatiotemporal organization is not constant, but instead tends to fluctuate, depending on the temporal intervals separating activation events among the various sites in the region. As soon as an activation event occurs in the epochal sequence, its associated activation pattern characterizes the spatiotemporal relationship of activations across all the sites that comprise that pattern, and this relationship can be compared to the spatiotemporal activation relationships inherent in adjacent activation patterns of the epochal sequence.

Translation of Activation Patterns to Spatiotemporal Patterns

With each increment of the activation pattern sequence, the amount of change that may occur from one activation pattern to the next is constrained. The degree of this constraint becomes more obvious following a translation of all the activation patterns associated with the epochal sequence to contain a common spatiotemporal reference, resulting in an epochal sequence of spatiotemporal patterns. In fact, such a translation facilitates the comparison of activation patterns.

For an epochal sequence of activation patterns to undergo translation, activation events associated with a specific site are made to be represented at a uniform position in both the spatial order and the temporal order of each translated activation pattern. The specific spatiotemporal reference may be selected for convenience of implementation. In the example cited previously using a catheter with 5 bipoles, the most proximal bipole may be assigned to be the spatial reference, and the translation result would manifest the first activation event to exist at this reference site within each translated activation pattern. The translation is accomplished as a modulo N operation. If the temporal position is X for the activation event associated with the spatial reference site in an activation pattern that is to be translated, then to translate said activation event to the first position of the temporal order, the following operation is performed on each temporal position Y in the activation pattern to obtain a translated result of temporal positions:

$$[Z_1, Z_2, \ldots, Z_N] = [(N-X+Y_1+1) \text{ modulo } N, \ldots, (N-X+Y_N+1) \text{ modulo } N] \ldots$$

for X, Y, and Z having identical domains: $\{1, 2, \ldots, N\}$. Since for each translated activation pattern, the spatiotemporal reference always will be in the same position of the spatial and temporal order for that pattern, it can be ignored; resultant spatiotemporal pattern labeling schemes thereby can be based upon the remaining $N-1$ sites and $N-1$ positions of temporal order.

FIG. 4A through FIG. 4F depict the 5 activation patterns that are related by virtue of pattern translation to the same unique spatiotemporal pattern. Note that FIG. 4A and FIG. 4F actually depict the same activation pattern, which has an associated spatiotemporal pattern; FIG. 4B through FIG. 4E depict the intermediate stepwise increments of the epochal sequence whereby all other activation patterns associated with that one spatiotemporal pattern also are manifest. In fact, for the 5 bipole sites depicted, there are 120 possible activations patterns, and 24 distinct spatiotemporal patterns. Generalizing for N sites, there are a total of N! possible activation patterns that theoretically may be detected, which translate into $(N-1)!$ unique spatiotemporal patterns; for each distinct spatiotemporal pattern, there exists N possible activation patterns, and these differ with respect to which site is labeled first in the associated activation patterns prior to translation.

The manner in which the sequence of activation patterns is determined conveniently constrains the degree to which a pattern can change within that sequence: the constraint is that in progressing from one activation pattern to the next pattern within the sequence, only the activation event succeeding the first activation event at its associated site within the pattern can shift its position with respect to the temporal order of the remaining sites in the next activation pattern. Even the extent of order change is finite and quantifiable; for N sites corresponding to N electrodes, an activation at a given site can shift anywhere from 0 to (N−1) positions in the temporal ordering of sites of the next activation pattern.

Pattern Analysis Methodology and Derived Metrics

The pattern labeling method of the present invention is central to the analytic metrics to be presented subsequently, which includes the following topics:

(1) Persistence Measurements (2) Measurement of Disorganization (3) Measurement of Asynchrony (4) Measurement of Nonrandomness (5) Analysis of Activation Pattern Distributions (6) Analysis of Pattern Trajectories Persistence Measurements An analysis of manifest activation pattern sequences provides a tool for evaluating the spatiotemporal organization of regional atrial activation during fibrillation.

Figure 3C:
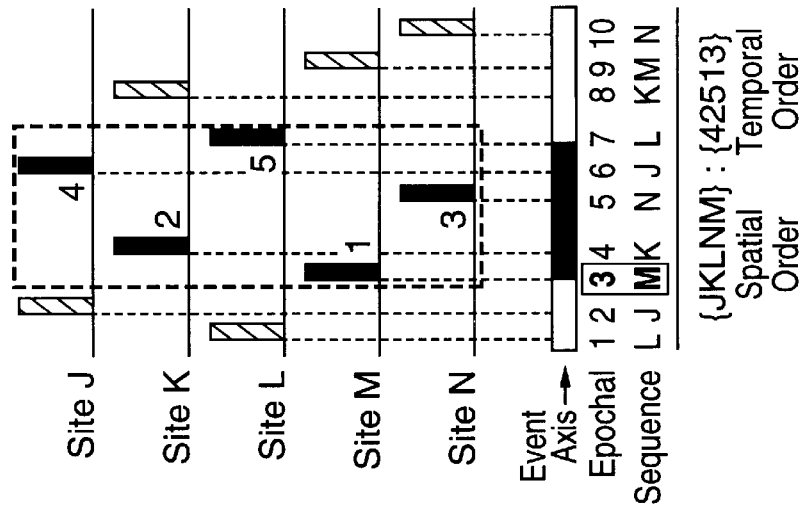
FIG. 3A through FIG. 3E are graphs illustrating activation pattern determination, and show activation event sequences for a regional set of sites [J, K, L, M, N], with the activation event sequence for each site obtained as depicted in FIG. 2A through FIG. 2C. Activation events from all sites are placed according to the order of their associated activation latencies into an epochal sequence, which is depicted at the bottom of each panel. Each activation event has an associated activation pattern.
Figure 3B:
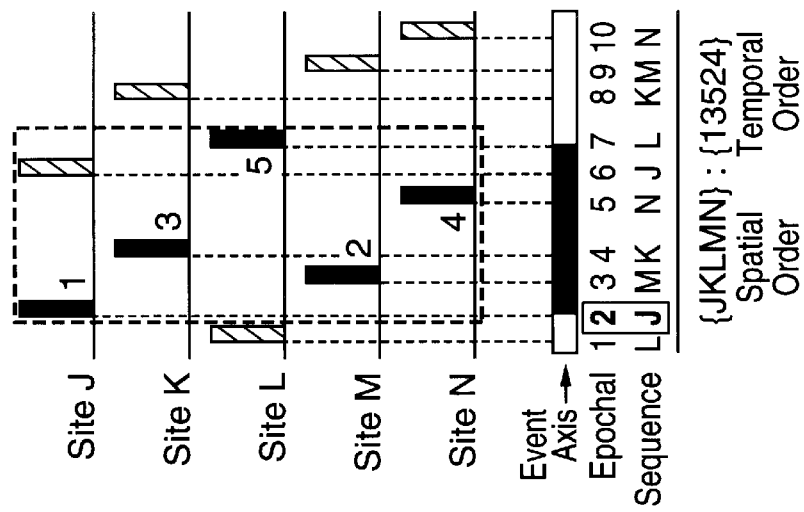
Figure 3A:
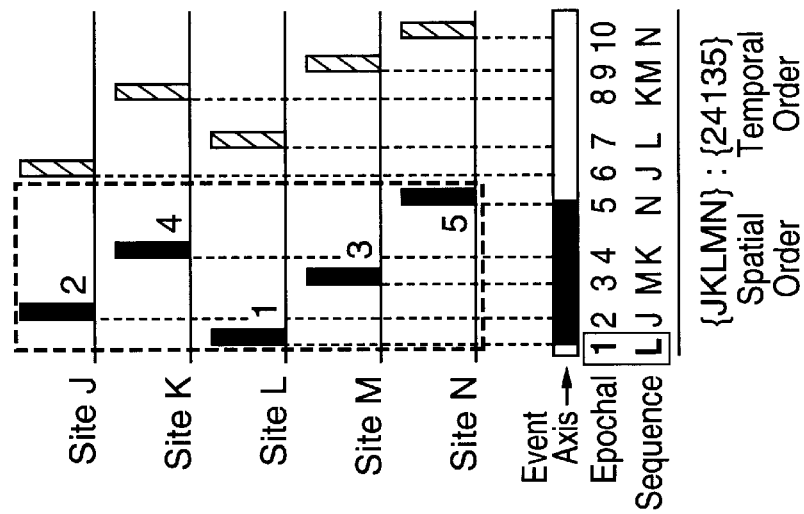
Figure 3E:
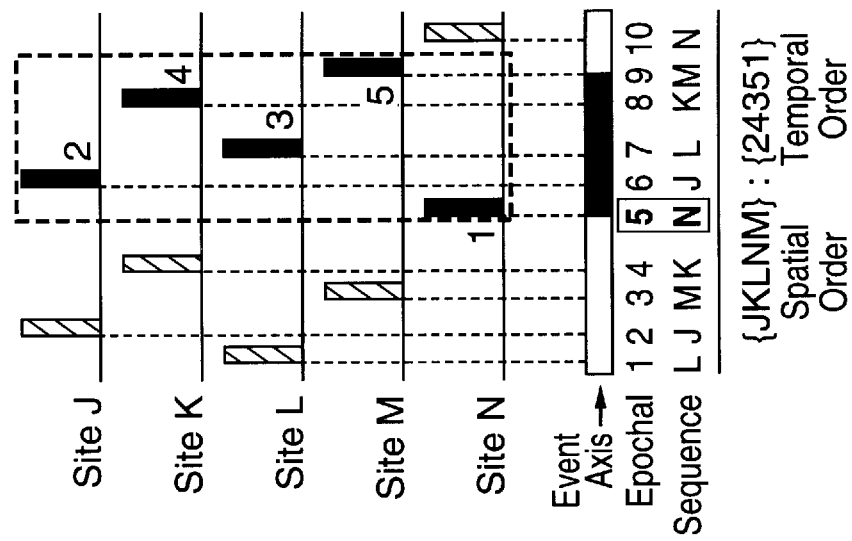
Figure 3D:
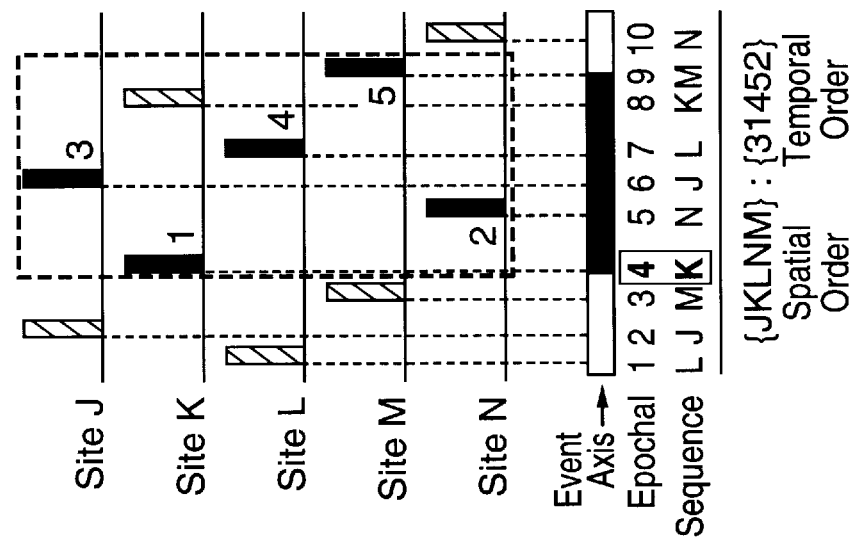
Figure 4C:
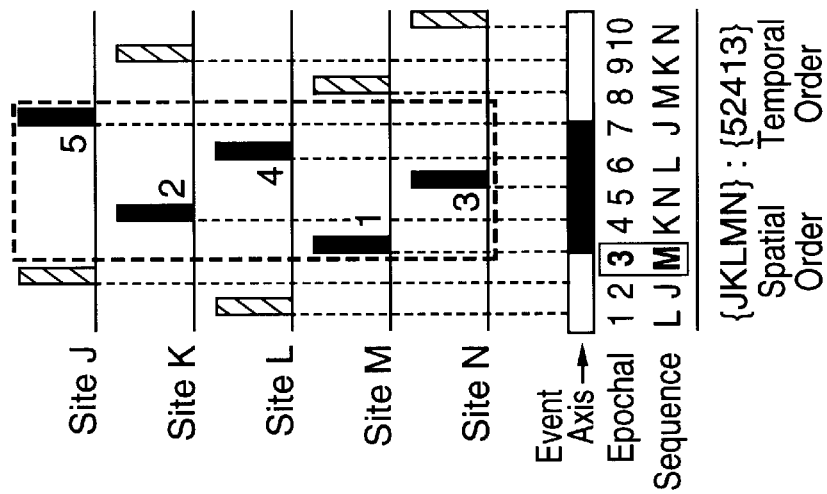
Figure 4B:
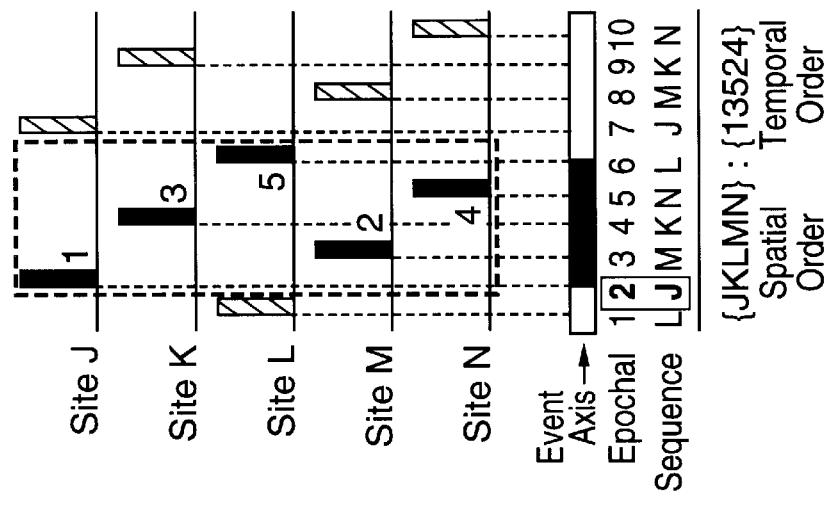
Figure 4A:
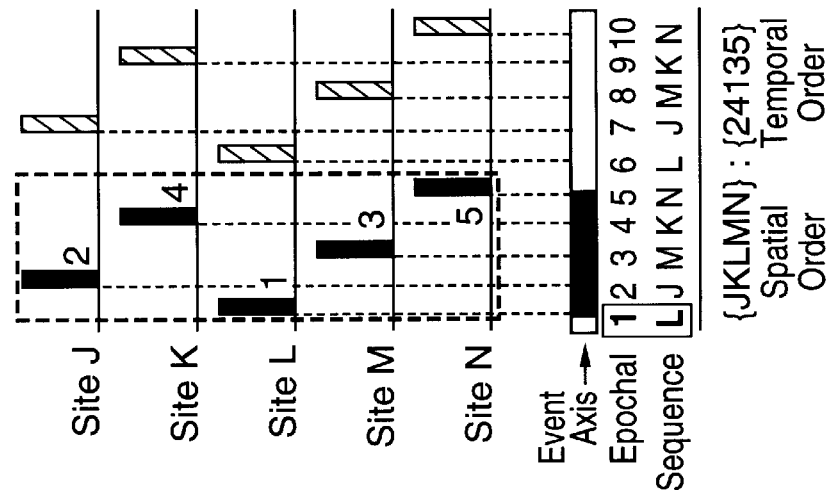
Figure 4F:
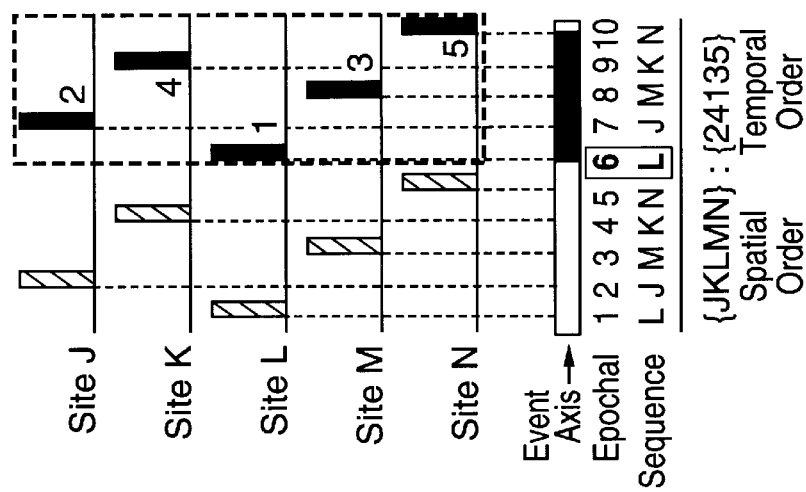
Figure 4E:
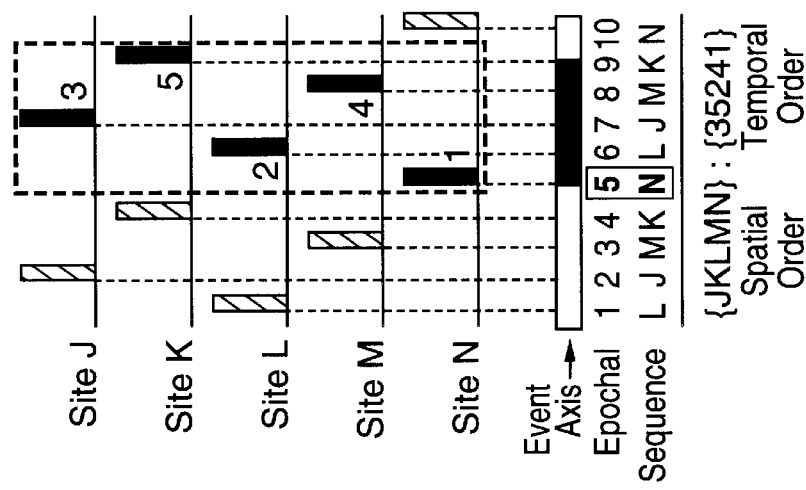
Figure 4D:
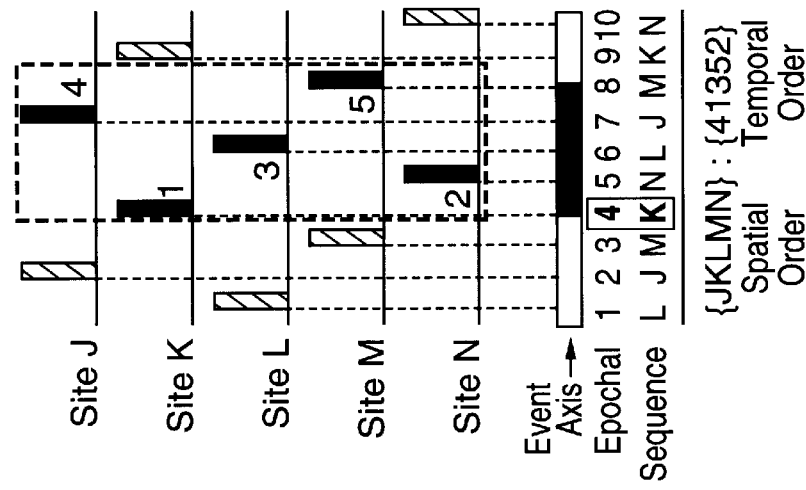

With the previous nomenclature describing sequential pattern analysis in mind, we can consider how patterns can be compared directly. In brief, patterns are compared by evaluating every possible pair of sites for a switch in the order of activation events that occur between successive spatiotemporal patterns in the epochal sequence. To facilitate such comparisons, it is convenient to translate the activation patterns to the vantage of a common spatiotemporal reference. Whenever the sequence of spatiotemporal patterns manifests repetition of a specific spatiotemporal pattern (or even a subset of patterns across a subregion), fibrillatory organization is evident. Persistence refers to this characteristic whereby two spatiotemporal patterns in a sequence remain unchanged. Accordingly, FIG. 4A through FIG. 4F illustrate persistence with each increment of the epochal sequence shown. In contrast, in FIG. 3A through FIG. 3E, only some of the increments in the sequence are persistent. The increments depicted from FIG. 3A to FIG. 3B, and from FIG. 3C to FIG. 3D, are persistent; the increments depicted from FIG. 3B to FIG. 3C, and from FIG. 3D to FIG. 3E, are not persistent.

Figure 5C:
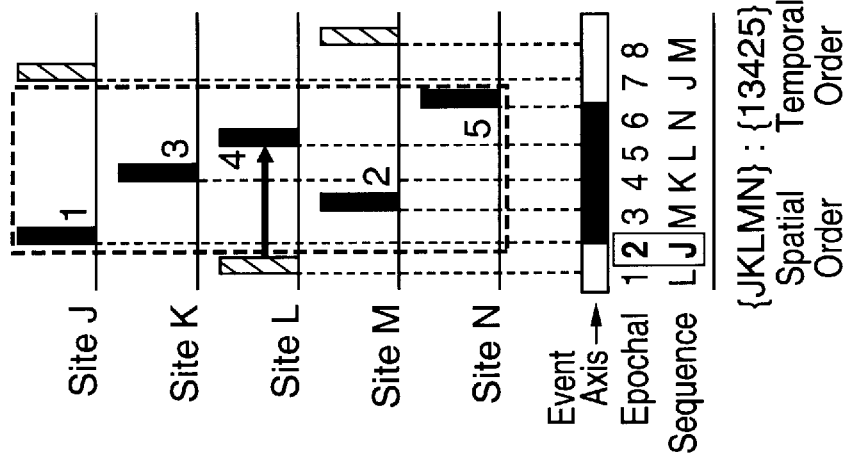
FIG. 5A through FIG. 5F are graphs illustrating emergence of an activation pattern from another.
Figure 5B:
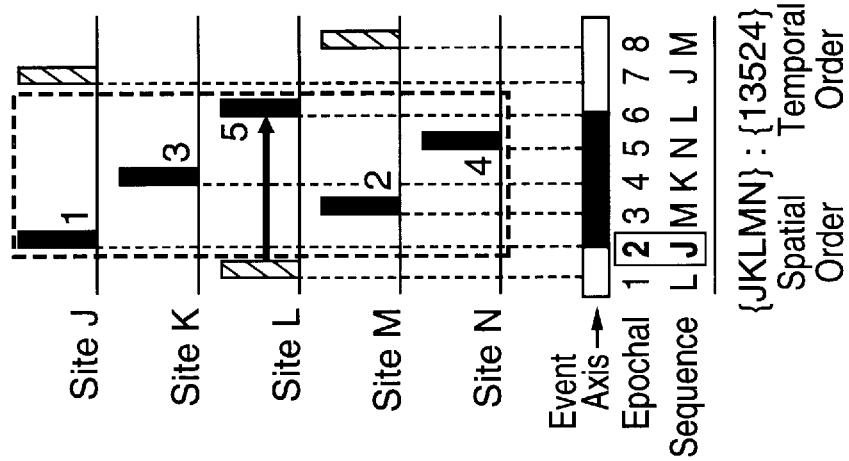
Figure 5A:
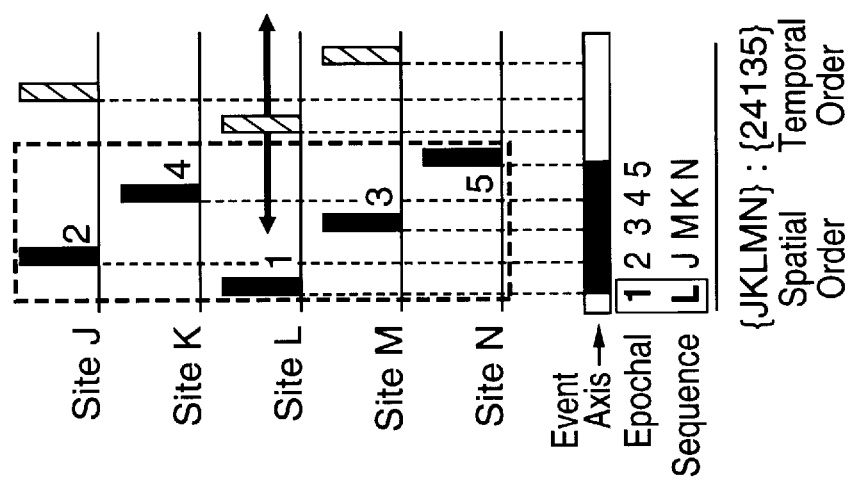

It should be noted that even if activation events were to be utterly random with respect to time and sampled location, the method of generating activation pattern sequences entails constraints as to how much change can occur between successive patterns. Usually, adjacent patterns in the sequence are compared. If this is the case, a constraint is imposed regarding what activation pattern can emerge from a specific activation pattern of the sequence. The first activation event of a specified activation pattern is replaced by the next activation event at the same site in the emerging activation pattern; this subsequent activation event may emerge anywhere in the temporal order of activation events of the remaining sites, but the order of these remaining sites with respect to each other is unchanged. As depicted in FIG. 5A and FIG. 5B (as well as in FIG. 4A through FIG. 4F), if the emerging position of the subsequent event occurs after the other activation events of the emerging activation pattern, then the result is an activation pattern which translates to the same spatiotemporal pattern as the activation pattern from which it emerged.

Figure 5F:
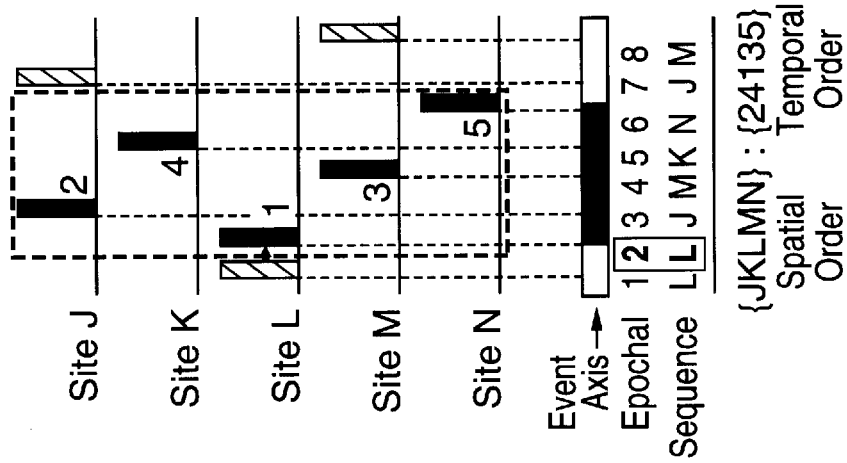
Figure 5E:
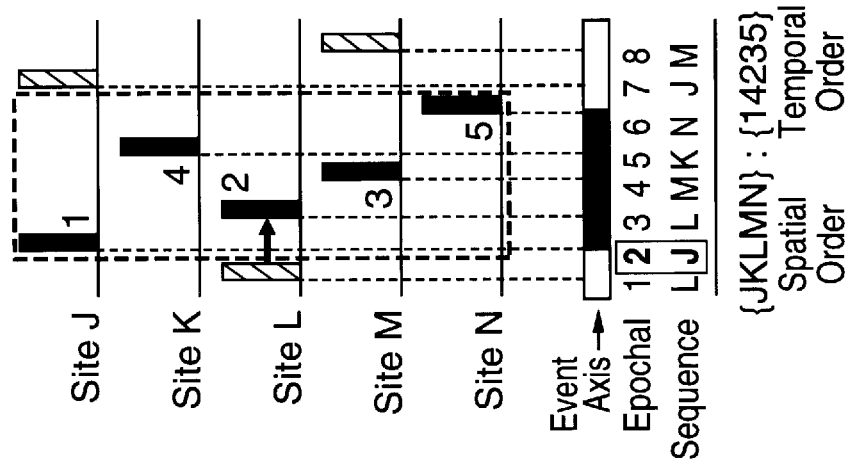
Figure 5D:
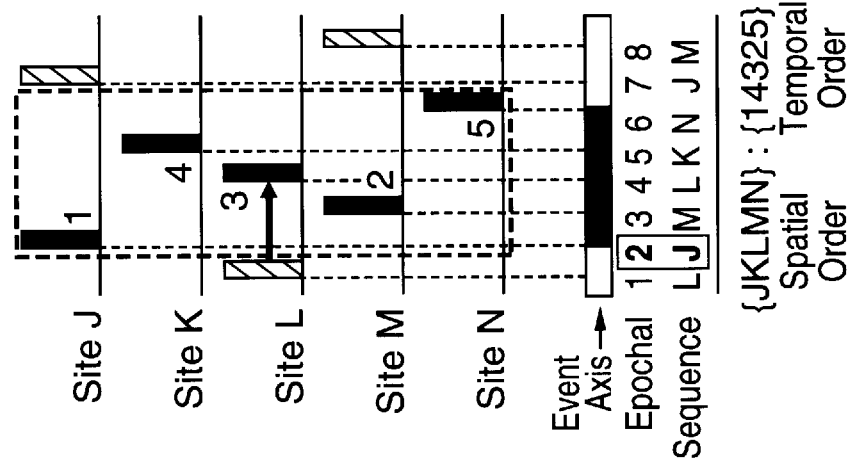

The emergence of the same spatiotemporal pattern from its preceding spatiotemporal pattern in the epochal sequence defines persistence; in contrast, if the spatiotemporal pattern changes, the associated increment in the spatiotemporal pattern sequence is nonpersistent. FIG. 5C through FIG. 5E depict the other possibilities for nonpersistent successive patterns emerging from the same activation pattern as that depicted in FIG. 5A. It may be noted further that if nonpersistence is manifest, the greater the number of positions from the last position in the emerging activation pattern that the newly emerged activation event occurs, the greater is the degree of pattern change introduced (the range being integers 0 to N−1, for N sites). FIG. 5F depicts an emerging activation pattern that is persistent with the activation pattern of FIG. 5A, but actually it represents a maximum extreme to the amount of order change that may exist between any two patterns. Accordingly, implementations of this invention may adjust for the occurrence of this extreme by registering the emergence of a nonpersistent activation pattern in such an instance; thus far, however, our experience in the analysis of atrial fibrillation has been that the occurrence of this maximal degree of order change is very infrequent.

Returning to the notion of the utter randomness of activation events with respect to sampled location and time, the persistence characteristic would be expected to be observed for approximately 1/Nth of the epochal sequence increments, if the epoch is of sufficient duration. If patterns are evaluated across multiple intervals of the spatiotemporal sequence under similar circumstances, fewer constraints to the emergence of other activation patterns exist, and consequently the likelihood of maintaining persistence over M sequence increments may be estimated by the ratio $((N-M)!/N!)$. Such estimates of randomness, whether or not reflective of a realizable electrophysiologic extreme, may serve as numeric values against which detected persistence can be compared for any specific and reproducible spatial arrangement of electrodes.

The opposite extreme is for the sequence of spatiotemporal patterns associated with perfectly organized rhythms, which manifest persistence throughout the entire epoch of measurement. Consequently, the general degree of spatiotemporal organization of an atrial region during fibrillation can be quantified by measuring the degree of persistence that exists between these two extremes. One metric, referred to as the persistence index, represents the ratio of persistent increments of the spatiotemporal pattern sequence to the total number of spatiotemporal pattern increments for the entire epochal sequence. The mean persistence metric represents the average number of consecutive increments of the spatiotemporal pattern sequence that remain persistent within a specified epoch.

Measurement of Disorganization

An alternative use of the sequential spatiotemporal pattern data is to quantify the amount of change that occurs between manifest spatiotemporal patterns, in association with each increment of the epochal sequence. Accordingly, we have developed a metric to measure the specific amount of order change from event to event.

As previously noted, for N electrodes, there are N discrete degrees of order change ranging from 0 to (N−1) that can occur from one spatiotemporal pattern to the next, reflecting the number of position shifts that occur between the successive patterns. The analogous term in the field of neural networks would be the Hamming distance. This quantifiable degree of shifting order allows for a discrete metric that records the amount of spatiotemporal order displacement. This order displacement is detectable at a relatively high temporal resolution, which is determined by the frequency of activation events occurring among all the sampled site locations; for every detected event from anywhere within the region, a new value quantifying discrete spatiotemporal pattern flux may be obtained, resulting in the disorganization metric. A value of zero is consistent with the occurrence of persistence for the associated increment of the epochal sequence. The maximum value (prior to any normalization) depends on the epochal sequence increment interval employed for each iteration (the iteration refers to the process of assigning a disorganization value to the occurrence of each activation event of the epochal sequence). For a sequence increment of one, the maximum number of possible order switches is equal to the number of bipoles being analyzed; however, as the event increment interval increases, the maximum number of possible order switches equals the total number of site pair combinations in the sampled region. The magnitude of this metric peaks only during any actual changes occurring in the sequence of spatiotemporal patterns.

Various schemes for further modification of this metric (and other metrics based on assessing changing patterns of activation) may be considered, as for example, in the case of nonuniform spatial sampling across a region. The magnitude of the resultant disorganization values (optionally normalized to the number of sampled sites for a result in the 0 to 1 range) may be graphed with respect to the sequential activation event count, or with respect to the temporal latencies associated with the activation events in the sequence.

Measurement of Asynchrony

Closely related to the disorganization metric is the asynchrony metric, which provides a quantification, from one activation pattern to the next, of the magnitude of the total change in the latency intervals between all possible pairs of sites in the region. The asynchrony metric is intended to provide a regionalized view of the fibrillatory process with a relatively high temporal resolution, while making no assumptions about statistical stationarity of the activation events.

For every detected event from anywhere within the spatially sampled region, an associated asynchrony value quantifies the total amount of change in the temporal relationships of activation events among all pairs of sites. With each increment of the epochal sequence, the temporal intervals between activation events associated with every possible pairing of sites in an activation pattern are compared with the temporal intervals between the next occurring activation events associated with the same site pairs; such a comparison provide a discrete estimate of first-ordered to provide a discrete estimate of first-order differences in manifest spatiotemporal order with respect to time and distance. In order to relate the asynchrony metric more closely to the physical geometry of the sampled sites, one variation of the metric allows for a spatial weighting term to be applied to each of the sites; shifts occurring closer to a reference site are weighted more heavily than those occurring further away. Also, a temporal normalization of the sequence of asynchrony values may be accomplished using the average of the activation cycle lengths for all sampled sites combined; the cycle length for an individual site, for instance, could be specified as the interval immediately following the latency associated with the activation event at that same site in the activation pattern under evaluation. This normalization renders the metric measurements approximately independent of activation rates, which may be important especially in the assessment of spatiotemporal organization during periods when acute perturbations are applied.

Figure 6A:
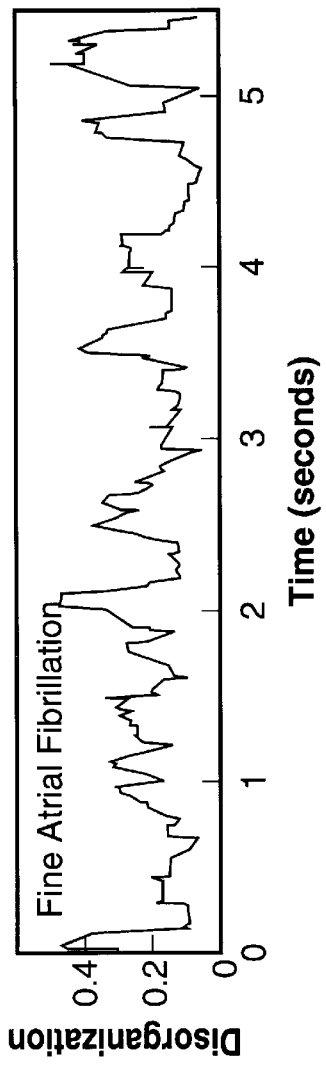
FIG. 6A through FIG. 6C are graphs illustrating asynchrony and show the results of a normalized asynchrony metric when applied to sets of electrograms for fine atrial fibrillation (FIG. 6A), coarse atrial fibrillation (FIG. 6B), and atrial flutter (FIG. 6C). The electrograms were obtained using five 1 mm bipoles spaced 1 cm apart along a single catheter positioned against the right atrial free wall endocardium.
Figure 6B:
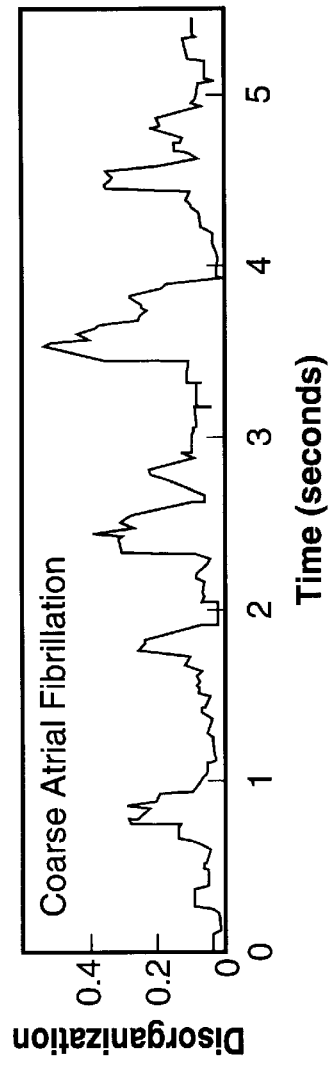
Figure 6C:
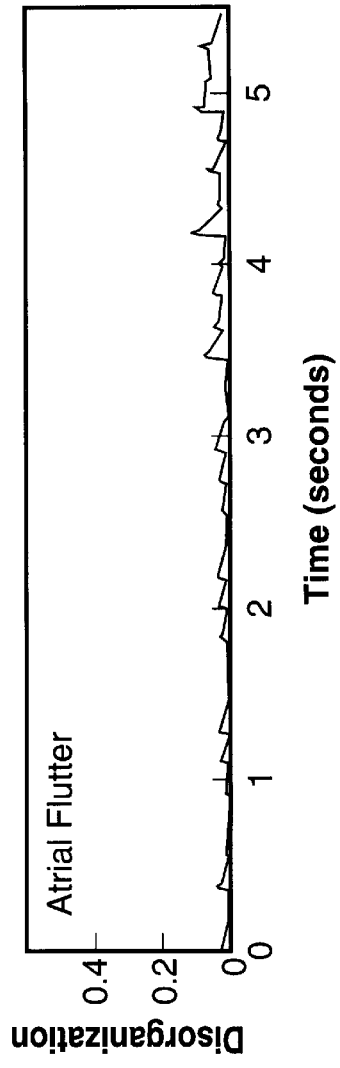
Figure 8A:
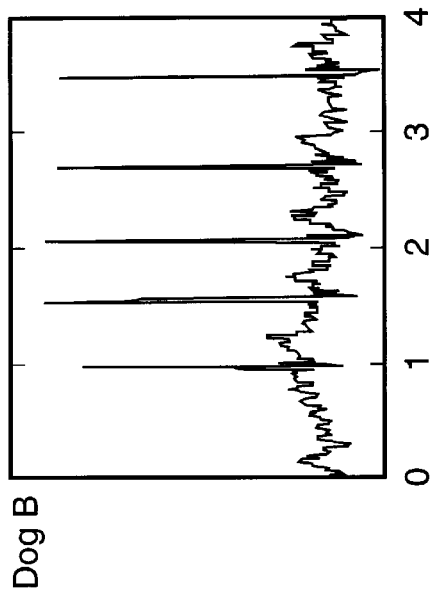
FIG. 8A through FIG. 8D are graphs showing surface ECGs corresponding to the atrial fibrillation analyzed in FIG. 7, and present 4-second ECG lead II epochs associated with each dog (A, B, C, and D, respectively) in FIG. 7 during atrial fibrillation.
Figure 8B:
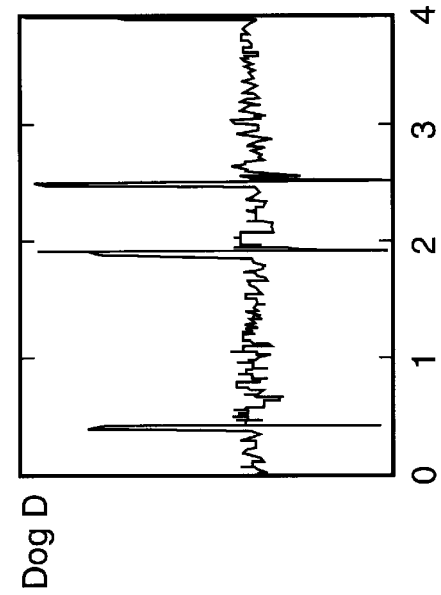
Figure 8C:
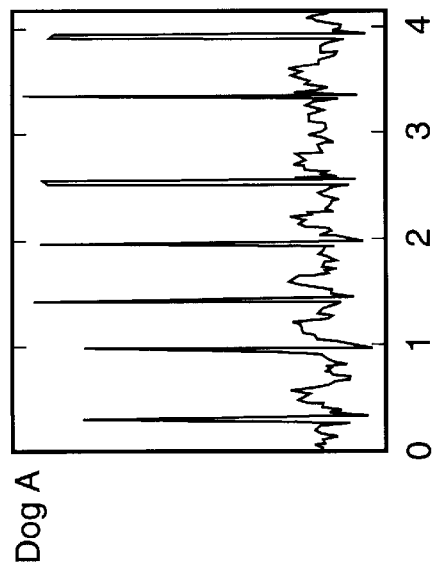
Figure 8D:
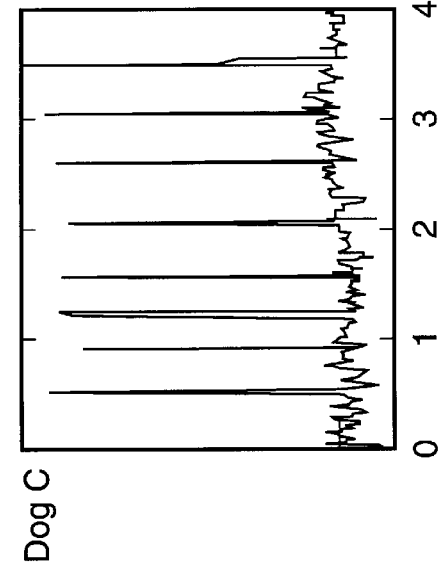

The time series created by plotting sequential values of the normalized asynchrony metric is a representation of the extent of spatiotemporal disorder present during the analysis interval. Because this asynchrony (or disorganization) sequence is calculated from activation events, it sometimes may be desirable to translate this metric back to the temporal domain by substituting the temporal latencies associated with each activation event, as shown in FIG. 6A through FIG. 6C, which present asynchrony curves computed from electrogram signals collected using five 1 mm bipoles spaced 1 cm apart along a single spline positioned at the anterolateral right atrial free wall. FIG. 6A corresponds to fine atrial fibrillation, FIG. 6B to coarse fibrillation, and FIG. 6C to atrial flutter.

The asynchrony metric provides a means to glimpse at dynamic time-varying characteristics of spatiotemporal fibrillatory structure, with or without rate dependence, and we wonder if it may be useful in timing the delivery of defibrillatory shocks.

Measurement of Nonrandomness

Persistence is indicative of spatiotemporal order, and specifically reflects linking behavior in atrial fibrillation, if it occurs more often than would be expected were the process utterly random. A second form of order involves oscillatory switching of the order of activation events associated with bipole pairs in successive spatiotemporal patterns. In this case, switching occurrences exceed the number of switches that otherwise might be expected in a random process. Such behavior observed for bipole pairs may reflect variable conduction block in the associated atrial region.

By associating pairs of sites within a region which are separated by identical distances, a curve can be constructed that depicts the proportion of spatiotemporal patterns across specified distances that are persistent relative to the number of unconstrained switching opportunities at each of those distances. Furthermore, multiple curves of this variety can be derived by comparing patterns at different increments along the epochal sequence (i.e. event intervals), with the curve approaching the persistence proportions that would be expected for a random process as the increment value is increased. Referring to FIG. 7, persistence curves are shown for four dogs (dogs A, B, C, and D) in atrial fibrillation having differing manifest degrees of STO, using an epochal sequence increment of 1. The persistence curves of FIG. 7 depict the ratio of persistent patterns to the total number of patterns as a function of bipole separation. Associated surface ECG leads acquired from these same four dogs are shown in FIG. 8A through FIG. 8D, respectively, each having a different degree of arrhythmia "coarseness" ranging from rapid atypical flutter (Dog A) to fine atrial fibrillation (Dog D). The dashed line in FIG. 7 shows the expected ratio of persistent activation patterns based on a statistical model of purely random activations. As the distance spanned by a pair of bipoles increases, there are more bipoles spanned by the pair, and the proportion of manifest persistent patterns decreases monotonically. Since it also is possible to describe the expected behavior of a random process, we can measure the area between the curve expected from a random process and the curve derived from actual data, and this area can be normalized to provide a measure of nonrandomness.

If the nonrandomness metric has a value of one, the patterns for all distances spanned by the bipole pairs are always persistent, indicative of a maximal degree of organization and spatiotemporal linkage, whereas a negative value is suggestive of oscillatory behavior dominating the process. A zero value is indicative of either randomness or a fine balance of persistence and oscillatory behavior during the epoch analyzed.

The nonrandomness metric is a unitless measure that with modification can be applied to a variety of bipole group arrangements, involving every possible pair combination of bipoles within their corresponding arrangements. On the other hand, it also can be used to measure more localized behavior specific to the atrial distance spanned by a specific pair of bipole sites, rather than the sum of all bipole sites spanning identical distances. Accordingly, these characteristics may allow for this analytic technique to be employed to search for areas along the atrial surface that demonstrate either persistence or oscillatory behavior out of proportion to neighboring regions.

Finally, this same technique can be employed to derive persistence duration curves for the distance spanned by any specified pair of bipoles in a regional arrangement of bipoles. These curves are constructed by utilizing a range of epochal sequence increments when advancing through the sequence of patterns, in a modified version of the method just discussed for measuring nonrandomness. The technique can be modified further to provide duration curves for a threshold magnitude of limited pair switching, rather than for the threshold of no switching, as in the case of persistent patterns. In fact, for a linear arrangement of bipoles, spatiotemporal organization could be characterized as a threshold-specific surface for depicting the likelihood of order switching exceeding that specified threshold as a discrete function of (1) distance between bipole pairs and (2) event intervals.

Analysis of Activation Pattern Distributions

In addition to examining activation pattern sequences, the observed distributions of activation patterns can be examined for additional insight regarding the spatiotemporal organization of fibrillatory activations. For example, certain spatiotemporal patterns may predominate over other patterns within the entire range of possible spatiotemporal patterns associated with a defined spatial set. For a set of N sampled sites in a region, there are exactly (N−1)! spatiotemporal patterns possible, as noted earlier. Accordingly, a statistical analysis of the distribution of manifest spatiotemporal patterns can be accomplished, and directly compared to a uniform distribution of spatiotemporal patterns, which would be expected were there an absence of structure to the spatiotemporal organization of fibrillation. Manifest pattern distributions in part may be result of: (1) the size of the atrial regions through which individual propagating wavefronts propagate before extinguishing or merging with other wavefronts, (2) an association of specific dominant patterns of activation with nearby regions of conduction block or sites of automatic activity, and (3) anisotropic conduction. We have been able to quantify distributions of these patterns from pilot study data, and have found that with multiple episodes of fibrillation in a given animal, there is a tendency for similar occurrences of pattern dominance.

As an example, we have applied this methodology to detect streaming of activation wavefronts. A linear arrangement of five equally spaced bipoles was positioned in an atrial region between suspected lines of conduction block in dogs with atrial fibrillation. We hypothesized that fibrillatory activation patterns in this region would not be completely random, due to the propagation constraints imposed by these lines of block. In analyzing the distribution of detected patterns that occurred, we looked for monotonically increasing and decreasing temporal ordering of the bipole sites; the occurrences of patterns with more than one bipole site out of monotonic sequence were notably under represented in comparison to what would be expected for utterly random distributions of activation sequences, indicative of streaming behavior. In addition, there was a tendency for the streaming to occur more often in one direction than the opposite direction for some of the study animals. Therefore, we are able to use this methodology not only to detect streaming, but also to obtain some idea regarding from where activation wavefronts preferentially may be emanating. The further refinement of this kind of analytic capability in the laboratory ultimately may permit fibrillatory mapping to identify specific foci or re-entrant circuits sustaining fibrillation that are thought to exist in some clinical instances. In fact, the use of regional persistence measurements, in combination with the simultaneous appearance of dominant patterns of activation, may be a particularly useful method to accomplish this.

Analysis of Pattern Trajectories

We also have begun to look in detail at the manifest sequences of activation patterns and how these patterns vary over time, applying the framework of this invention to the study of pattern trajectories in an effort to gain a better understanding of how (and where) activation patterns terminate and re-emerge. Although this method is particularly sensitive to any inaccuracies in the determination of activation events, pattern trajectory analysis is expected to provide additional insights regarding manifest constraints on regional fibrillatory behavior.

The methodology of the proposed invention imposes a finite number of possibilities for what activation patterns can follow from another specific activation pattern. Even if a full range of evenly distributed spatiotemporal patterns were to be manifest during fibrillation, a degree of order from within a region yet may be detectable by virtue of a higher order analysis of the epochal sequence of activation patterns.

Rather than analyzing the occurrence of specific activation patterns or spatiotemporal patterns, trajectories of activation patterns are analyzed. An activation pattern emerging from, or dissipating into, a subsequent activation pattern of the epochal sequence is the simplest manifestation of a first order activation pattern trajectory; a finite number of 1st order trajectories exists for a specified number of spatial sites sampling a region of interest. An analysis of the manifest sequence of 1st order trajectories, as well as the associated statistical distributions of these 1st order trajectories, provides yet another means for characterizing the spatiotemporal organization of fibrillation.

In fact, within the limitations imposed by the epoch length of the acquired signals and the accuracy with which the activation events accurately reflect the true local activation latencies at the regional sites sampled, similar analyses may be accomplished for higher order trajectory analyses. For example, a first order trajectory emerging from, or dissipating into, a subsequent 1st order trajectory of the epochal sequence is the simplest manifestation of a second order activation pattern trajectory; again, a finite number of 2nd order trajectories exists for a specified number of spatial sites sampling a region of interest. An analysis of the manifest sequence of 2nd order trajectories, as well as the associated statistical distributions of these 2nd order trajectories, provides yet another means for characterizing the spatiotemporal organization of fibrillation. Further extension of this technique provides the means for even higher order analyses.

Figure 9:
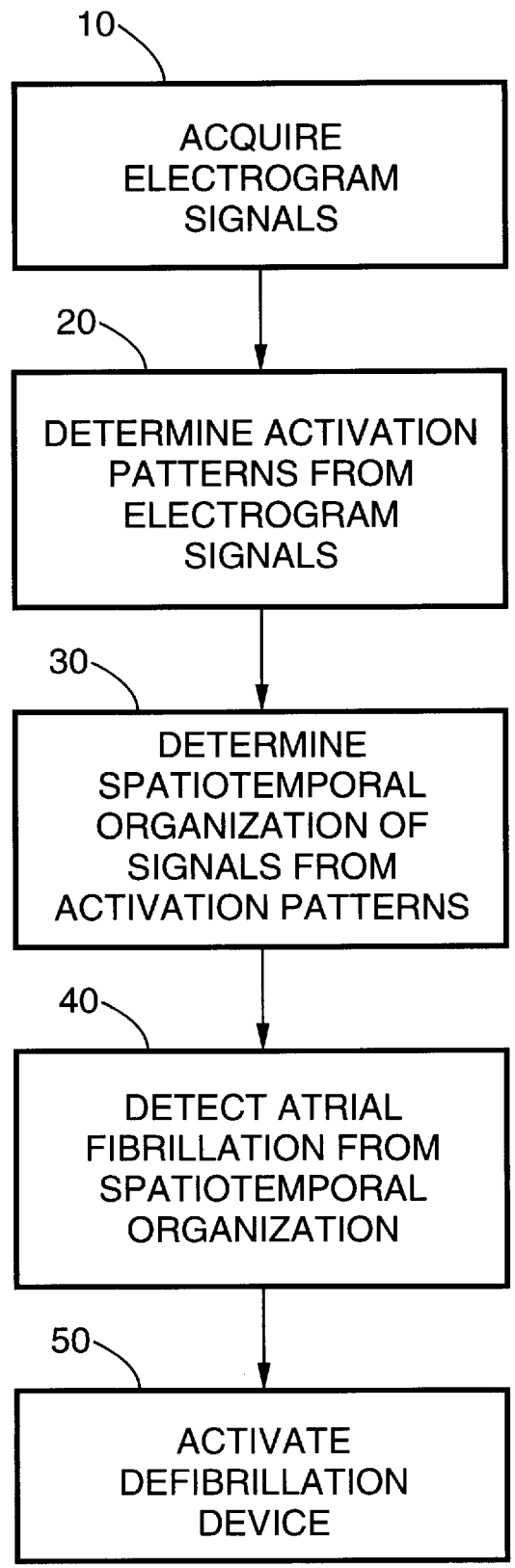
FIG. 9 is a flow chart showing a method for detecting atrial fibrillation in accordance with the invention.

Greater insight into the structure of fibrillatory STO may be obtained through the combination of various trajectory analyses of different order. This information, perhaps in combination with similar analyses in other atrial regions, may allow for a specific enough characterization of atrial fibrillation that may lead to short-term predictions of subsequent activation patterns to be manifest. Additionally, with the availability of detailed information regarding fibrillatory structure available for atrial regions of interest, an analysis of the phasic relationships of fibrillatory structure simultaneously analyzed in different regions may provide a an effective means for a step-wise localization of foci or re-entrant circuits that perhaps drive atrial fibrillation, causing it to sustain. Referring to FIG. 9, an example of a method for detecting atrial fibrillation in accordance with the present invention is shown. At step 10, electrogram signals are acquired from a plurality of sites. At step 20, activation patterns of the signals are determined. At step 30, spatiotemporal organization is determined from the activation patterns. At step 40, the presence of atrial fibrillation is determined from the spatiotemporal organization. If necessary of desired, a defribillation device is activated at step 50. It will be appreciated the foregoing steps and their sequence may vary without departing from the basic concepts as disclosed herein, and that the invention can include additional steps as described herein.

Accordingly, it will be seen that this invention provides metrics for characterizing and quantifying the spatiotemporal structure of electrical propagation during atrial (or ventricular) fibrillation. These metrics, primarily derived from electrograms, are based on the representation of fibrillatory wavefronts as ordered sequences of activation events. Preliminary evaluation of these metrics in both animals and a computer model of atrial fibrillation not only has demonstrated their ability to differentiate atrial fibrillation from atrial flutter and other regular rhythms, but also has demonstrated the ability to differentiate subtle degrees of spatiotemporal structure during episodes of fibrillation. Furthermore, consistent regional differences in atrial fibrillatory structure reproducibly have been demonstrated in both animals and a computer model of atrial fibrillation as a result of this invention.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A method for characterizing the spatiotemporal organization of atrial fibrillation, comprising the steps of:
   (a) acquiring electrogram signals during atrial fibrillation from a plurality of sites adjacent to a region of atrial tissue;
   (b) determining activation patterns from said electrogram signals; and
   (c) determining spatiotemporal organization of electrical propagation from said activation patterns.

2. A method as recited in claim 1, further comprising the step of detecting atrial fibrillation from said spatiotemporal organization.

3. A method as recited in claim 1, further comprising the step of activating a defibrillation device in response to detection of specific characteristics of said spatiotemporal organization.

4. A method for detecting and characterizing the spatiotemporal organization of atrial fibrillation based upon the spatiotemporal relationship of activation events detected at sites representing spatial samples within an atrial region of interest, comprising the steps of:
   (a) simultaneously acquiring electrogram signals during atrial fibrillation from a plurality of sites adjacent to a region of atrial tissue;
   (b) determining the latencies of the activation events at each site;
   (c) determining sequences of activation patterns from said activation event latencies; and
   (d) translating said sequences of activation patterns to sequences of spatiotemporal patterns having a common spatiotemporal reference.

5. A method as recited in claim 4, further comprising the step of detecting atrial fibrillation from said sequences of spatiotemporal patterns.

6. A method as recited in claim 4, further comprising the step of activating a defibrillation device in response to detection of specific characteristics of said sequences of spatiotemporal patterns.

7. A method for detecting and characterizing the spatiotemporal organization of atrial fibrillation based upon the spatiotemporal relationship of activation events detected at sites representing spatial samples within an atrial region of interest, comprising the steps of:
   (a) simultaneously acquiring electrogram signals during atrial fibrillation from a plurality of sites adjacent to a region of atrial tissue;
   (b) determining activation events at each site from said electrogram signals;
   (c) determining sequences of activation patterns from said activation events; and
   (d) determining spatiotemporal organization of electrical propagation within said atrial region of interest from said sequences of activation patterns wherein atrial fibrillation is detected and characterized from said spatiotemporal organization.

8. A method as recited in claim 7, wherein said step of determining said spatiotemporal organization includes the step of deriving said spatiotemporal organization from a manifest sequence of said activation patterns.

9. A method as recited in claim 7, wherein said step of determining said spatiotemporal organization includes the step of deriving said spatiotemporal organization from a manifest statistical distribution of said activation patterns.

10. A method as recited in claim 7, wherein said step of determining said spatiotemporal organization includes the step of deriving said spatiotemporal organization from a manifest trajectory of said activation patterns.

11. A method as recited in claim 7, wherein said step of determining said spatiotemporal organization includes the step of deriving said spatiotemporal organization from a manifest sequence and manifest statistical distribution of said activation patterns.

12. A method as recited in claim 7, wherein said step of determining said spatiotemporal organization includes the step of deriving said spatiotemporal organization from a manifest sequence and manifest trajectory of said activation patterns.

13. A method as recited in claim 7, wherein said step of determining said spatiotemporal organization includes the step of deriving said spatiotemporal organization from a manifest sequence of spatiotemporal patterns derived from said activation patterns.

14. A method as recited in claim 7, wherein said step of determining said spatiotemporal organization includes the step of deriving said spatiotemporal organization from a manifest statistical distribution of spatiotemporal patterns derived from said activation patterns.

15. A method as recited in claim 7, wherein said step of determining said spatiotemporal organization includes the step of deriving said spatiotemporal organization from a manifest trajectory of spatiotemporal patterns derived from said activation patterns.

16. A method as recited in claim 7, wherein said step of determining activation events comprises the steps of:
  (a) screening the acquired signals and excluding signals having high noise levels or poor signal quality; and
  (b) filtering the screened signals, and obtaining a resultant set of time series having peaks at the latencies of maximal energy within a prescribed upper frequency bandwidth, wherein said peaks occur at times that define activation events associated with the original signals.

17. A method as recited in claim 7, wherein said step of determining sequences of activation patterns from said activation events comprises the steps of:
  (a) placing together in temporal order all activation events that have been detected from a set of electrodes positioned at the atrial region; and
  (b) determining an activation pattern associated with each event, whereby an event is assigned to be in a consistent temporal position within its associated activation pattern, and then uniformly determining the temporal sequence of activation events for a consistent spatial ordering of the sites within the region of interest.

18. A method as recited in claim 7, wherein said step of determining sequences of activation patterns from said activation events comprises the steps of:
  (a) placing together in temporal order all activation events that have been detected from a set of electrodes positioned at the atrial region; and
  (b) determining an activation pattern associated with each event, whereby each event is assigned to be in a consistent spatial position within its associated activation pattern, and then uniformly determining the spatial sequence of activation events for a consistent temporal ordering of the sites within the region of interest.

19. A method as recited in claim 17, further comprising the step of translating the sequence of activation patterns to a sequence of spatiotemporal patterns having a common spatiotemporal reference.

20. A method as recited in claim 18, further comprising the step of translating the sequence of activation patterns to a sequence of spatiotemporal patterns having a common spatiotemporal reference.

21. A method as recited in claim 7, wherein said step of determining spatiotemporal organization of electrical propagation from manifest sequences of activation patterns comprises the steps of:
  (a) deriving a sequence of spatiotemporal patterns from the activation patterns;
  (b) comparing each spatiotemporal pattern with subsequent patterns in the sequence to determine the presence or absence of a pattern match across a range of spatiotemporal pattern sequence increments;
  (c) computing a quantitative spatiotemporal organization characterization based upon the relative proportion of pattern stability across a range of distances that separate subgroupings; and
  (d) plotting said characterization of sampled distances vs. activation event increment vs. proportion of spatiotemporal pattern stability, to provide information that can be compared to expected plots associated with random spatiotemporal activation.

22. A method as recited in claim 7, further comprising the step of detecting atrial fibrillation from said spatiotemporal organization.

23. A method as recited in claim 7, further comprising the step of activating a defibrillation device in response to detection of atrial fibrillation.

24. A method as recited in claim 7, further comprising the step of activating a defibrillation device in response to the detection of specific characteristics of the spatiotemporal organization of atrial fibrillation.

25. A method as recited in claim 8, wherein said step of determining spatiotemporal organization of electrical propagation from a manifest sequence of activation patterns comprises the steps of:
  (a) deriving a sequence of spatiotemporal patterns from the activation patterns;
  (b) comparing each spatiotemporal pattern with its subsequent spatiotemporal pattern in the sequence to determine the presence or absence of a pattern match; and
  (c) computing a metric result based upon the proportion of sequential matching of spatiotemporal patterns.

26. A method as recited in claim 8, wherein said step of determining spatiotemporal organization of electrical propagation from a manifest sequence of activation patterns comprises the steps of:
  (a) deriving a sequence of spatiotemporal patterns from the activation patterns;
  (b) comparing each spatiotemporal pattern with its subsequent pattern in the sequence to quantify the amount of order change occurring amongst all sites; and
  (c) computing a metric result based upon the amount of spatiotemporal order change that occurs with each subsequent increment of the spatiotemporal pattern sequence.

27. A method as recited in claim 8, wherein said step of determining spatiotemporal organization of electrical propagation from a manifest sequence of activation patterns comprises the steps of:
  (a) deriving a sequence of spatiotemporal patterns from the activation patterns;
  (b) evaluating each spatiotemporal pattern with another pattern occurring at a specified increment in the sequence of spatiotemporal patterns to determine the presence or absence of a spatiotemporal pattern match; and
  (c) computing a metric result based on the proportion of sequential matching of spatiotemporal patterns at the specified increment.

28. A method as recited in claim 8, wherein said step of determining spatiotemporal organization of electrical propagation from a manifest sequence of activation patterns comprises the steps of:
  (a) deriving a sequence of spatiotemporal patterns from the activation patterns;
  (b) evaluating each spatiotemporal pattern with all other spatiotemporal patterns occurring within a specified increment of the sequence of spatiotemporal patterns, to determine the presence or absence of any change among the spatiotemporal patterns within that interval; and
  (c) computing a metric result based upon the proportion of spatiotemporal patterns in the sequence for which all associated spatiotemporal patterns within the increment interval remain unchanged.

29. A method as recited in claim 8, wherein said step of determining spatiotemporal organization of electrical propagation from a manifest sequence of activation patterns comprises the steps of:
  (a) mathematically comparing the temporal intervals between activation events associated with every possible pairing of sites in an activation pattern with the temporal intervals between activation events associated with the corresponding site pairs of a subsequent activation pattern in the sequence; and (b) deriving a metric result quantifying spatiotemporal organization from a function of the comparison values so derived.

30. A method as recited in claim 8, wherein said step of determining spatiotemporal organization of electrical propagation from a manifest sequence of activation patterns comprises the steps of:

(a) mathematically comparing the temporal intervals between activation events associated with every possible pairing of sites in an activation pattern with the temporal intervals between the next occurring activation events associated with the same site pairs; and (b) deriving a metric result quantifying spatiotemporal organization from a function of the comparison values so derived.

31. A method as recited in claim 30, wherein said step of deriving a metric result quantifying spatiotemporal organization from a function of the derived comparison values comprises the steps of:

(a) calculating the absolute value of the difference between the temporal interval associated with activations at a pair of sites in an activation pattern and the corresponding temporal interval for activations at those same sites in a subsequent pattern that is comprised of the next occurring activation events, for every possible pairing of sites in said activation pattern;

(b) summating said absolute values associated with the site pairings of an activation pattern, and doing so for successive activation patterns in the sequence; and (c) deriving a metric result from said summations to quantify spatiotemporal organization.

32. A method as recited in claim 31, wherein said step of deriving a metric result from said summations to quantify spatiotemporal organization may include temporal normalization of the metric result, comprising the steps of:

(a) calculating the temporal interval between an activation event of an activation pattern and the next activation event at that same site, for each site of the activation pattern;

(b) deriving a temporal normalization factor from the mean of the intervals so derived for every site of an activation pattern;

(c) dividing the summation associated with each activation pattern by the temporal normalization factor associated with that same activation pattern to obtain temporally normalized summation values; and (d) deriving a metric result from said temporally normalized summation values to quantify spatiotemporal organization.

33. A method as recited in claim 8, wherein said step of determining spatiotemporal organization of electrical propagation from a manifest sequence of activation patterns comprises the steps of:

(a) mathematically comparing the temporal intervals between activation events associated with every possible pairing of sites in an activation pattern with the temporal intervals between the previous occurring activation events associated with the same site pairs; and (b) deriving a metric result quantifying spatiotemporal organization from a function of the comparison values so derived.

34. A method as recited in claim 33, wherein said step of deriving a metric result quantifying spatiotemporal organization from a function of the derived comparison values comprises the steps of:

(a) calculating the absolute value of the difference between the temporal interval associated with activations at a pair of sites in an activation pattern and the corresponding temporal interval for activations at those same sites in a subsequent pattern that is comprised of the previous occurring activation events, for every possible pairing of sites in said activation pattern;

(b) summating said absolute values associated with the site pairings of an activation pattern, and doing so for successive activation patterns in the sequence; and (c) deriving a metric result from said summations to quantify spatiotemporal organization.

35. A method as recited in claim 34, wherein said step of deriving a metric result from said summations to quantify spatiotemporal organization may include temporal normalization of the metric result, comprising the steps of:

(a) calculating the temporal interval between an activation event of an activation pattern and the previous activation event at that same site, for each site of the activation pattern;

(b) deriving a temporal normalization factor from the mean of the intervals so derived for every site of an activation pattern;

(c) dividing the summation associated with each activation pattern by the temporal normalization factor associated with that same activation pattern to obtain temporally normalized summation values; and (d) deriving a metric result from said temporally normalized summation values to quantify spatiotemporal organization.

36. A method as recited in claim 9, wherein said step of determining spatiotemporal organization of electrical propagation from a manifest statistical distribution of activation patterns comprises the steps of:

(a) analyzing the statistical distributions of the observed activation patterns in relation to the entire range of activation patterns that exists for the specified number of spatial sites being considered; and (b) deriving a metric result based upon a statistical description of said distributions.

37. A method as recited in claim 9, wherein said step of determining spatiotemporal organization of electrical propagation from a manifest statistical distribution of activation patterns comprises the steps of:

(a) deriving spatiotemporal patterns from the activation patterns;

(b) analyzing the statistical distributions of the observed spatiotemporal patterns in relation to the entire range of spatiotemporal patterns that exists for the specified number of spatial sites being considered; and (c) deriving a metric result based upon a statistical description of said distribution.

38. A method as recited in claim 9, wherein said step of determining spatiotemporal organization of electrical propagation from a manifest statistical distribution of activation patterns comprises the steps of:

(a) analyzing the distributions of the observed activation patterns in relation to the entire range of activation patterns that exists for the specific number of spatial sites being considered, to identify relative proportions within the distributions of one or more subgroupings of related activation patterns; and (b) deriving a metric result based upon said proportions.

39. A method as recited in claim 9, wherein said step of determining spatiotemporal organization of electrical propagation from a manifest statistical distribution of activation patterns comprises the steps of:

(a) deriving spatiotemporal patterns from the activation patterns;

(b) analyzing the distributions of the observed spatiotemporal patterns in relation to the entire range of spatiotemporal patterns that exists for the specific number of spatial sites being considered, to identify relative proportions within the distributions of one or more subgroupings of related spatiotemporal patterns; and (c) deriving a metric result based upon said proportions.

40. A method as recited in claim 9, wherein said step of determining spatiotemporal organization of electrical propagation from a manifest statistical distribution of activation patterns comprises the steps of:

(a) analyzing the relative distributions of the observed activation patterns to identify the manifestation of the preferential occurrence of activation patterns; and (b) deriving a metric result based upon the predominance of a particular activation pattern.

41. A method as recited in claim 9, wherein said step of determining spatiotemporal organization of electrical propagation from a manifest statistical distribution of activation patterns comprises the steps of:

(a) deriving spatiotemporal patterns from the activation patterns;

(b) analyzing the relative distributions of the observed spatiotemporal patterns to identify the manifestation of the preferential occurrence of spatiotemporal patterns; and (c) deriving a metric result based upon the predominance of a particular spatiotemporal pattern.

42. A method as recited in claim 9, wherein said step of determining spatiotemporal organization of electrical propagation from a manifest statistical distribution of activation patterns comprises the steps of:

(a) analyzing the relative distributions of the observed activation patterns to identify the manifestation of the preferential occurrence of related subgroupings of activation patterns; and (b) deriving a metric result based upon the predominance of a particular related subgrouping of activation patterns.

43. A method as recited in claim 9, wherein said step of determining spatiotemporal organization of electrical propagation from a manifest statistical distribution of activation patterns comprises the steps of:

(a) deriving spatiotemporal patterns from the activation patterns;

(b) analyzing the relative distributions of the observed spatiotemporal patterns to identify the manifestation of the preferential occurrence of related subgroupings of spatiotemporal patterns; and (c) deriving a metric result based upon the predominance of a particular related subgrouping of spatiotemporal patterns.

44. A method as recited in claim 11, wherein said step of determining spatiotemporal organization of electrical propagation from a manifest sequence and manifest statistical distribution of said activation patterns, comprises the steps of:

(a) deriving spatiotemporal patterns from the activation patterns;

(b) comparing each spatiotemporal pattern with its subsequent pattern in the sequence to determine the presence or absence of a pattern match;

(c) analyzing the relative distributions of the observed spatiotemporal patterns in relation to the entire range of spatiotemporal patterns that exists for the specific number of spatial sites being considered, to identify the manifestation of the preferential occurrence of spatiotemporal patterns; and (d) deriving a metric result based upon the predominance of a particular spatiotemporal pattern which quantifies the relationship of pattern dominance to the occurrence of matching sequential spatiotemporal patterns.

45. A method as recited in claim 9, wherein said step of determining spatiotemporal organization of electrical propagation from a manifest sequence and manifest statistical distribution of said activation patterns, comprises the steps of:

(a) deriving spatiotemporal patterns from the activation patterns;

(b) comparing each spatiotemporal pattern with its subsequent pattern in the sequence to determine the presence or absence of a pattern match;

(c) analyzing the relative distributions of the observed spatiotemporal patterns in relation to the entire range of spatiotemporal patterns that exists for the specific number of spatial sites being considered, to identify the manifestation of the preferential occurrence of related subgroupings of spatiotemporal patterns; and (d) deriving a metric result based upon the predominance of a particular related subgrouping of spatiotemporal patterns which quantifies the relationship of pattern dominance to the occurrence of matching sequential spatiotemporal patterns.

46. A method as recited in claim 12, wherein said step of determining spatiotemporal organization of electrical propagation from a manifest sequence and trajectory of said activation patterns, comprises the steps of:

(a) analyzing the statistical distributions of the observed increments in the sequence of activation patterns in relation to the entire range of possible increments that exists for the specified number of spatial sites being considered; and (b) deriving a metric result based upon a numeric and/or graphical description of said distributions.

47. A method as recited in claim 12, wherein said step of determining spatiotemporal organization of electrical propagation from a manifest sequence and trajectory of said activation patterns, comprises the steps of:

(a) analyzing the statistical distributions of the observed increments in the sequence of activation patterns in relation to the entire range of possible increments that exists for the specified number of spatial sites being considered; and (b) deriving a metric result based upon a numeric and/or graphical description of the relative proportions of particular related trajectory subgroupings.

48. A method as recited in claim 12, wherein said step of determining spatiotemporal organization of electrical propagation from a manifest sequence and trajectory of said activation patterns, comprises the steps of:

(a) analyzing the statistical distributions of the observed increments in the sequence of activation patterns to identify relative proportions of the emergence of specific activation patterns from other activation patterns, including the same activation pattern; and (b) deriving a metric result based upon a numeric description of said distributions, a graphical description of said distributions, or both a numeric and graphical description of said distributions.

49. A method as recited in claim 12, wherein said step of determining spatiotemporal organization of electrical propagation from a manifest sequence and trajectory of said activation patterns, comprises the steps of:

(a) analyzing the statistical distribution of the observed increments in the sequence of activation patterns to identify relative proportions of the dissipation of each specific activation pattern into other specific activation patterns, including the same activation pattern; and (b) deriving a metric result based upon a numeric description of said distributions, a graphical description of said distributions, or both a numeric and graphical description of said distributions.

50. A method as recited in claim 12, wherein said step of determining spatiotemporal organization of electrical propagation from a manifest sequence and trajectory of said activation patterns, comprises the steps of:

(a) analyzing the statistical distribution of the observed increments in the sequence of activation patterns to identify relative proportions of the emergence of each specific activation pattern from other specific activation patterns, including the same activation pattern; and (b) deriving a metric result based upon a numeric description of said distributions, a graphical description of said distributions, or both a numeric and graphical description of the predominance of a particular related subgrouping of trajectories.

51. A method as recited in claim 12, wherein said step of determining spatiotemporal organization of electrical propagation from a manifest sequence and trajectory of said activation patterns, comprises the steps of:

(a) analyzing the statistical distribution of the observed increments in the sequence of activation patterns to identify relative proportions of the dissipation of each specific activation pattern into other specific activation patterns, including the same activation pattern; and (b) deriving a metric result based upon a numeric description of said distributions, a graphical description of said distributions, or both a numeric and graphical description of the predominance of a particular related subgrouping of trajectories.

52. A method for mapping atrial fibrillation by assessing spatiotemporal organization at multiple targeted atrial regions, comprising the steps of:

(a) simultaneously acquiring electrogram signals during atrial fibrillation from a plurality of sites adjacent to each targeted region of atrial tissue;

(b) determining activation events at each site from said electrogram signals;

(c) determining sequences of activation patterns for each targeted region from the activation events associated with that region;

(d) determining spatiotemporal organization of electrical propagation within each targeted atrial region from sequences of activation patterns associated with that region; and (e) comparing spatiotemporal organization in different atrial regions wherein atrial fibrillation can be detected and characterized from said comparison.

53. A method as recited in claim 52, further comprising the step of detecting atrial fibrillation from said spatiotemporal organization regional comparison.

54. A method as recited in claim 52, further comprising the step of activating a defibrillation device in response to detection of specific characteristics of said spatiotemporal organization regional comparison.

* * * * *